(12) United States Patent
Rome et al.

(10) Patent No.: US 7,578,803 B2
(45) Date of Patent: Aug. 25, 2009

(54) MULTIFUNCTION ADAPTOR FOR AN OPEN-ENDED CATHETER

(75) Inventors: Guy T. Rome, West Valley City, UT (US); William R. Barron, Riverton, UT (US); John G. Evans, South Jordon, UT (US); Dwight Hibdon, Park City, UT (US); John A. Zawacki, Park City, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 25 days.

(21) Appl. No.: 11/076,564

(22) Filed: Mar. 8, 2005

(65) Prior Publication Data

US 2005/0261664 A1  Nov. 24, 2005

Related U.S. Application Data

(63) Continuation-in-part of application No. 10/803,512, filed on Mar. 18, 2004.

(51) Int. Cl.
*A61M 5/178* (2006.01)
(52) U.S. Cl. .............................. 604/167.04; 604/167.03; 604/533
(58) Field of Classification Search ......... 604/244–249, 604/256–258, 533–539, 523, 164.01–164.13, 604/167.01–167.06; 606/108
See application file for complete search history.

(56) References Cited

U.S. PATENT DOCUMENTS

| | | | |
|---|---|---|---|
| 3,176,690 | A | 4/1965 | H'Doubler |
| D217,795 | S | 6/1970 | Spaven |
| 3,805,794 | A | 4/1974 | Schlesigner |
| 4,000,739 | A | 1/1977 | Stevens |
| 4,068,659 | A | 1/1978 | Moorehead |
| 4,198,973 | A | 4/1980 | Millet |
| 4,233,974 | A | 11/1980 | Desecki et al. |
| 4,296,747 | A | 10/1981 | Ogle |
| 4,306,562 | A | 12/1981 | Osborne |
| 4,411,654 | A | 10/1983 | Boarini et al. |
| 4,412,832 | A | 11/1983 | Kling et al. |
| 4,424,833 | A | 1/1984 | Spector et al. |
| 4,430,081 | A | 2/1984 | Timmermans |

(Continued)

FOREIGN PATENT DOCUMENTS

EP  1240916 A1  9/2002

(Continued)

OTHER PUBLICATIONS

Camp, "Care of the Groshong Catheter", Oncol Nurs Forum, vol. 15, No. 6, 1988.

(Continued)

*Primary Examiner*—Nicholas D Lucchesi
*Assistant Examiner*—Theodore J Stigell
(74) *Attorney, Agent, or Firm*—Rutan & Tucker LLP

(57) ABSTRACT

A multifunction adaptor for an open-ended catheter that allows placement of the catheter while minimizing the risk of air embolism or blood loss through the open (proximal) end of the catheter body. In one variation, the design allows passage of a standard guidewire for "over-the-guidewire" placement techniques and a connection for catheter flushing using a standard syringe. In another variation, the multifunction adaptor is configured for coupling a tunneler to the proximal end of a catheter.

15 Claims, 15 Drawing Sheets

U.S. PATENT DOCUMENTS

| | | |
|---|---|---|
| 4,431,426 A | 2/1984 | Groshong et al. |
| 4,436,519 A | 3/1984 | O'Neill |
| 4,445,893 A | 5/1984 | Bodicky |
| 4,449,973 A | 5/1984 | Luther |
| 4,468,224 A | 8/1984 | Enzmann et al. |
| 4,473,067 A | 9/1984 | Schiff |
| RE31,855 E | 3/1985 | Osborne |
| 4,557,261 A | 12/1985 | Riiheimer |
| 4,571,241 A | 2/1986 | Christopher |
| 4,581,012 A | 4/1986 | Brown et al. |
| 4,581,025 A | 4/1986 | Timmermans |
| 4,591,355 A | 5/1986 | Hilse |
| 4,596,559 A | 6/1986 | Fleischhacker |
| 4,610,665 A | 9/1986 | Matsumoto et al. |
| 4,619,643 A | 10/1986 | Bai |
| 4,626,245 A | 12/1986 | Weinstein |
| 4,650,472 A | 3/1987 | Bates |
| 4,673,393 A | 6/1987 | Suzuki et al. |
| 4,701,159 A | 10/1987 | Brown et al. |
| 4,722,725 A * | 2/1988 | Sawyer et al. ................. 604/27 |
| 4,723,550 A | 2/1988 | Bales et al. |
| 4,726,374 A | 2/1988 | Bales et al. |
| 4,743,265 A | 5/1988 | Whitehouse et al. |
| 4,747,833 A | 5/1988 | Kousai et al. |
| 4,753,765 A | 6/1988 | Pande |
| 4,772,266 A | 9/1988 | Groshong |
| 4,784,644 A | 11/1988 | Sawyer et al. |
| 4,795,426 A | 1/1989 | Jones |
| 4,798,594 A | 1/1989 | Hillstead |
| 4,842,592 A | 6/1989 | Caggiani et al. |
| 4,865,593 A | 9/1989 | Ogawa et al. |
| 4,909,798 A | 3/1990 | Fleischhacker et al. |
| 4,921,479 A | 5/1990 | Grayzel |
| 4,929,235 A | 5/1990 | Merry et al. |
| 4,929,236 A | 5/1990 | Sampson |
| 4,932,633 A | 6/1990 | Johnson et al. |
| 4,935,010 A | 6/1990 | Cox et al. |
| 4,936,826 A | 6/1990 | Amarasinghe |
| 4,946,133 A | 8/1990 | Johnson et al. |
| 4,952,359 A | 8/1990 | Wells |
| 4,960,412 A | 10/1990 | Fink |
| 4,966,588 A | 10/1990 | Rayman et al. |
| 4,983,168 A | 1/1991 | Moorehead |
| 4,997,424 A | 3/1991 | Little |
| 5,007,901 A | 4/1991 | Shields |
| 5,035,686 A | 7/1991 | Crittenden et al. |
| 5,041,095 A | 8/1991 | Littrell |
| 5,053,014 A | 10/1991 | Van Heugten |
| 5,064,414 A | 11/1991 | Revane |
| 5,066,285 A | 11/1991 | Hillstead |
| 5,071,411 A | 12/1991 | Hillstead |
| 5,078,688 A | 1/1992 | Lobodzinski et al. |
| 5,085,645 A | 2/1992 | Purdy et al. |
| 5,092,857 A | 3/1992 | Fleischhacker |
| 5,098,392 A | 3/1992 | Fleischhacker et al. |
| 5,098,393 A | 3/1992 | Amplatz et al. |
| 5,108,380 A * | 4/1992 | Herlitze et al. ............... 604/533 |
| 5,112,301 A | 5/1992 | Fenton, Jr. et al. |
| 5,114,408 A | 5/1992 | Fleischhaker et al. |
| 5,117,836 A | 6/1992 | Millar |
| 5,125,904 A | 6/1992 | Lee |
| 5,141,497 A | 8/1992 | Erskine |
| 5,149,327 A | 9/1992 | Oshiyama |
| 5,154,701 A | 10/1992 | Cheer et al. |
| 5,158,545 A | 10/1992 | Trudell et al. |
| 5,160,323 A | 11/1992 | Andrew |
| 5,163,903 A | 11/1992 | Crittenden et al. |
| 5,167,634 A | 12/1992 | Corrigan, Jr. et al. |
| 5,167,637 A | 12/1992 | Okada et al. |
| 5,169,393 A | 12/1992 | Moorehead et al. |
| 5,171,222 A | 12/1992 | Euteneuer et al. |
| 5,180,372 A | 1/1993 | Vegoe et al. |
| 5,190,529 A | 3/1993 | McCrory et al. |
| 5,191,898 A | 3/1993 | Millar |
| 5,197,976 A | 3/1993 | Herweck et al. |
| 5,201,722 A | 4/1993 | Moorehead et al. |
| 5,205,834 A | 4/1993 | Moorehead et al. |
| 5,211,633 A | 5/1993 | Stouder, Jr. |
| 5,215,538 A | 6/1993 | Larkin |
| 5,221,263 A | 6/1993 | Sinko et al. |
| 5,234,410 A | 8/1993 | Graham et al. |
| 5,242,413 A | 9/1993 | Heiliger |
| 5,242,430 A | 9/1993 | Arenas et al. |
| 5,250,033 A | 10/1993 | Evans et al. |
| 5,255,691 A | 10/1993 | Otten |
| 5,273,540 A | 12/1993 | Luther et al. |
| 5,273,546 A | 12/1993 | McLaughlin et al. |
| 5,275,583 A | 1/1994 | Crainich |
| 5,279,597 A | 1/1994 | Dassa et al. |
| 5,290,294 A | 3/1994 | Cox et al. |
| 5,304,142 A | 4/1994 | Liebl et al. |
| 5,312,355 A | 5/1994 | Lee |
| 5,312,357 A | 5/1994 | Buijs et al. |
| 5,320,602 A | 6/1994 | Karpiel |
| 5,324,271 A | 6/1994 | Abiuso et al. |
| 5,334,157 A | 8/1994 | Klein et al. |
| 5,334,187 A | 8/1994 | Fischell et al. |
| 5,336,192 A | 8/1994 | Palestrant |
| 5,348,537 A | 9/1994 | Wiesner et al. |
| 5,350,362 A | 9/1994 | Stouder, Jr. |
| 5,350,363 A | 9/1994 | Goode et al. |
| 5,364,393 A | 11/1994 | Auth et al. |
| 5,368,574 A | 11/1994 | Antonacci et al. |
| 5,382,241 A | 1/1995 | Choudhury et al. |
| 5,389,090 A | 2/1995 | Fischell et al. |
| 5,391,152 A | 2/1995 | Patterson |
| 5,395,352 A | 3/1995 | Penny |
| 5,397,311 A | 3/1995 | Walker et al. |
| 5,405,320 A | 4/1995 | Twardowski et al. |
| 5,405,323 A | 4/1995 | Rogers et al. |
| 5,409,463 A | 4/1995 | Thomas et al. |
| 5,409,464 A | 4/1995 | Villalobos |
| 5,409,469 A | 4/1995 | Schaerf |
| 5,413,561 A | 5/1995 | Fischell et al. |
| 5,419,340 A | 5/1995 | Stevens |
| 5,423,762 A | 6/1995 | Hillstead |
| 5,429,616 A | 7/1995 | Schaffer |
| 5,437,645 A | 8/1995 | Urban et al. |
| 5,441,504 A | 8/1995 | Pohndorf et al. |
| 5,453,095 A | 9/1995 | Davila et al. |
| 5,460,616 A | 10/1995 | Weinstein et al. |
| 5,472,418 A | 12/1995 | Palestrant |
| 5,472,435 A | 12/1995 | Sutton |
| 5,474,099 A | 12/1995 | Boehmer et al. |
| 5,484,401 A | 1/1996 | Rodriguez |
| 5,488,960 A | 2/1996 | Toner |
| 5,496,346 A | 3/1996 | Horzewski et al. |
| 5,501,676 A | 3/1996 | Niedospial et al. |
| 5,509,897 A | 4/1996 | Twardowski et al. |
| 5,520,655 A | 5/1996 | Davila et al. |
| 5,536,255 A | 7/1996 | Moss |
| 5,538,505 A | 7/1996 | Weinstein et al. |
| 5,542,931 A * | 8/1996 | Gravener et al. ....... 604/167.03 |
| 5,599,305 A | 2/1997 | Hermann et al. |
| 5,613,953 A | 3/1997 | Pohndorf |
| 5,613,956 A | 3/1997 | Patterson et al. |
| 5,647,857 A | 7/1997 | Anderson et al. |
| 5,653,698 A | 8/1997 | Niedospial et al. |
| 5,672,158 A | 9/1997 | Okada et al. |
| 5,685,856 A | 11/1997 | Lehrer |
| 5,702,370 A | 12/1997 | Sylvanowicz et al. |
| 5,713,867 A | 2/1998 | Morris |
| 5,735,819 A | 4/1998 | Elliott |
| 5,741,233 A | 4/1998 | Riddle et al. |

| | | |
|---|---|---|
| 5,752,937 A | 5/1998 | Otten et al. |
| 5,755,693 A | 5/1998 | Walker et al. |
| 5,755,702 A | 5/1998 | Hillstead et al. |
| 5,766,203 A | 6/1998 | Imran et al. |
| 5,772,678 A | 6/1998 | Thomason et al. |
| 5,782,807 A | 7/1998 | Falvai et al. |
| 5,782,817 A | 7/1998 | Franzel et al. |
| 5,800,414 A | 9/1998 | Cazal |
| 5,843,031 A | 12/1998 | Hermann et al. |
| 5,853,393 A | 12/1998 | Bogert |
| 5,858,007 A | 1/1999 | Fagan et al. |
| 5,879,333 A | 3/1999 | Smith |
| 5,885,217 A | 3/1999 | Gisselberg et al. |
| 5,895,376 A | 4/1999 | Schwartz et al. |
| 5,911,710 A | 6/1999 | Barry et al. |
| 5,916,194 A | 6/1999 | Jacobsen et al. |
| 5,919,160 A | 7/1999 | Sanfilippo, II |
| 5,921,968 A | 7/1999 | Lampropoulos et al. |
| 5,935,112 A | 8/1999 | Stevens et al. |
| 5,944,695 A | 8/1999 | Johnson et al. |
| 5,951,518 A | 9/1999 | Licata et al. |
| 5,957,912 A | 9/1999 | Heitzmann |
| 5,967,490 A | 10/1999 | Pike |
| 5,971,958 A | 10/1999 | Zhang |
| 6,024,729 A | 2/2000 | Dehdashtian et al. |
| 6,027,480 A | 2/2000 | Davis et al. |
| 6,033,375 A | 3/2000 | Brumbach |
| 6,033,388 A | 3/2000 | Nordstrom et al. |
| 6,053,904 A | 4/2000 | Scribner et al. |
| 6,074,377 A | 6/2000 | Sanfilippo, II |
| 6,083,207 A | 7/2000 | Heck |
| 6,086,570 A | 7/2000 | Aboul-Hosn et al. |
| 6,088,889 A | 7/2000 | Luther et al. |
| 6,106,540 A | 8/2000 | White et al. |
| 6,120,476 A | 9/2000 | Fung et al. |
| 6,120,480 A | 9/2000 | Zhang et al. |
| 6,142,981 A * | 11/2000 | Heck et al. ............... 604/256 |
| 6,159,198 A | 12/2000 | Gardeski et al. |
| 6,162,196 A | 12/2000 | Hart et al. |
| 6,171,281 B1 | 1/2001 | Zhang |
| 6,210,366 B1 | 4/2001 | Sanfilippo, II |
| 6,213,988 B1 | 4/2001 | McIvor et al. |
| 6,221,057 B1 | 4/2001 | Schwartz et al. |
| 6,228,062 B1 | 5/2001 | Howell et al. |
| 6,258,058 B1 | 7/2001 | Sanfilippo, II |
| 6,273,871 B1 | 8/2001 | Davis et al. |
| 6,276,661 B1 | 8/2001 | Laird |
| 6,322,541 B2 | 11/2001 | West et al. |
| 6,331,176 B1 | 12/2001 | Becker et al. |
| 6,338,725 B1 | 1/2002 | Hermann et al. |
| 6,344,033 B1 * | 2/2002 | Jepson et al. ............... 604/256 |
| 6,352,520 B1 | 3/2002 | Miyazaki |
| 6,402,723 B1 | 6/2002 | Lampropoulos et al. |
| 6,413,250 B1 | 7/2002 | Smith |
| 6,454,744 B1 | 9/2002 | Spohn et al. |
| 6,458,103 B1 | 10/2002 | Albert et al. |
| 6,494,860 B2 | 12/2002 | Rocamora et al. |
| 6,497,681 B1 | 12/2002 | Brenner |
| 6,508,790 B1 | 1/2003 | Lawrence |
| 6,520,939 B2 | 2/2003 | Lafontaine |
| 6,544,247 B1 | 4/2003 | Gardeski et al. |
| 6,551,283 B1 | 4/2003 | Guo et al. |
| 6,575,960 B2 | 6/2003 | Becker et al. |
| 6,589,262 B1 | 7/2003 | Honebrink et al. |
| 6,592,544 B1 | 7/2003 | Mooney et al. |
| 6,623,460 B1 | 9/2003 | Heck |
| 6,632,200 B2 | 10/2003 | Guo et al. |
| 6,638,242 B2 | 10/2003 | Wilson et al. |
| 6,645,178 B1 | 11/2003 | Junker et al. |
| 6,663,595 B2 | 12/2003 | Spohn et al. |
| 6,682,498 B2 | 1/2004 | Ross |
| 6,682,519 B1 | 1/2004 | Schon |
| 6,692,464 B2 | 2/2004 | Graf |
| 6,695,832 B2 | 2/2004 | Schon et al. |
| 6,719,749 B1 | 4/2004 | Schweikert et al. |
| 6,827,710 B1 | 12/2004 | Mooney et al. |
| 6,872,198 B1 | 3/2005 | Wilson et al. |
| 6,881,211 B2 | 4/2005 | Schweikert et al. |
| 6,887,220 B2 | 5/2005 | Hogendijk |
| 6,916,313 B2 | 7/2005 | Cunningham |
| 6,921,396 B1 * | 7/2005 | Wilson et al. ............... 604/508 |
| 2001/0041873 A1 | 11/2001 | Dopper et al. |
| 2002/0128604 A1 * | 9/2002 | Nakajima ............... 604/164.01 |
| 2004/0065333 A1 | 4/2004 | Wilson et al. |
| 2004/0092863 A1 | 5/2004 | Raulerson et al. |
| 2004/0097903 A1 | 5/2004 | Raulerson |
| 2004/0122418 A1 | 6/2004 | Voorhees |
| 2004/0158208 A1 | 8/2004 | Hiejima |
| 2004/0167478 A1 | 8/2004 | Mooney et al. |
| 2004/0171997 A1 | 9/2004 | Wilson et al. |
| 2004/0172003 A1 | 9/2004 | Wilson et al. |
| 2004/0176739 A1 | 9/2004 | Stephens et al. |
| 2004/0186444 A1 | 9/2004 | Daly et al. |
| 2004/0193119 A1 * | 9/2004 | Canaud et al. ............... 604/247 |
| 2004/0243095 A1 | 12/2004 | Nimkar et al. |
| 2005/0049555 A1 | 3/2005 | Moorehead et al. |
| 2005/0113805 A1 | 5/2005 | Devellian et al. |

FOREIGN PATENT DOCUMENTS

| | | |
|---|---|---|
| WO | WO 97/22374 | 6/1997 |
| WO | WO 00/23137 | 4/2000 |

OTHER PUBLICATIONS

Delmore et al., "Experience with the Groshong Long-Term Central Venous Catheter", Gynecologic Oncology 34, 216-218 (1989).

Malviya et al., "Vascular Access in Gynecological Cancer Using the Groshong Right Atrial Catheter", Gynecological Oncology 33, 313-316 (1989).

*Health Devices* May-Jun. 1998; 25(5-6):214-5.

* cited by examiner

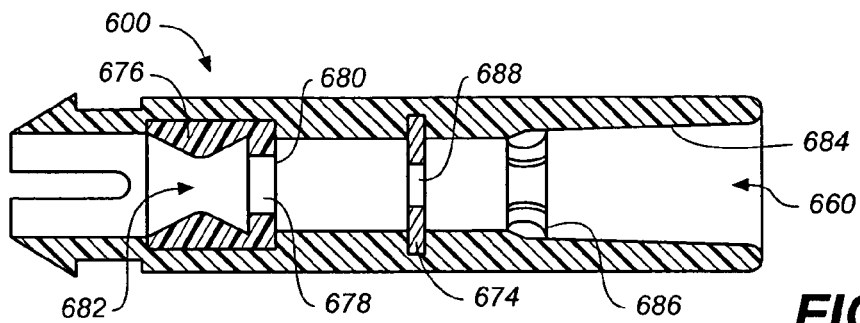
*FIG. 12A*
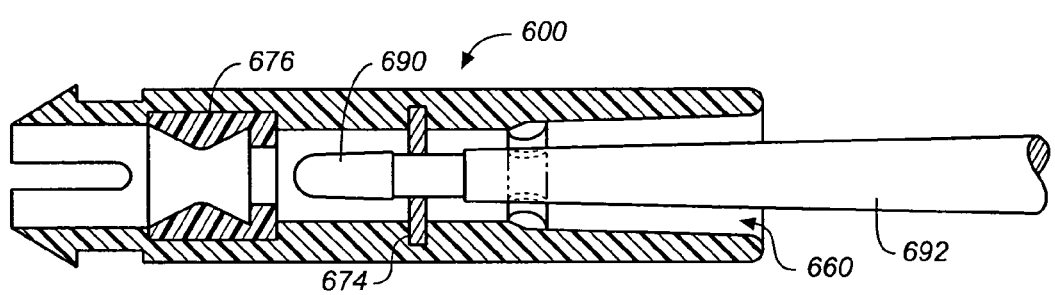
*FIG. 12B*
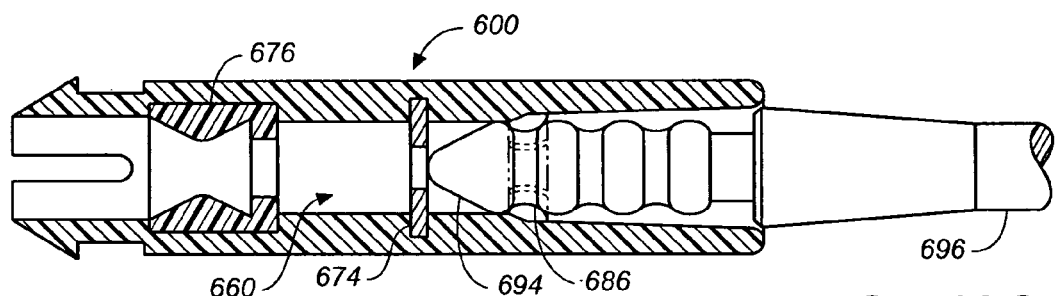
*FIG. 12C*
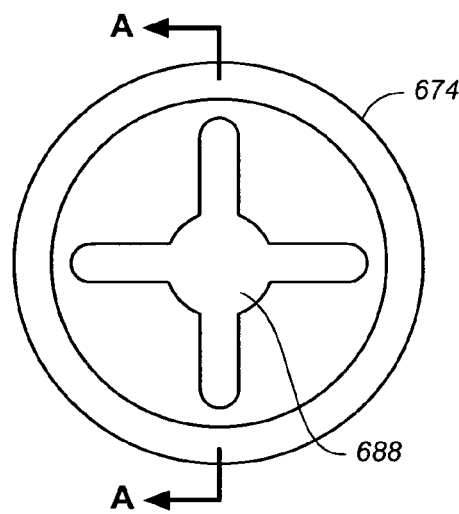 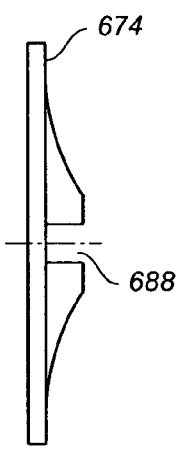 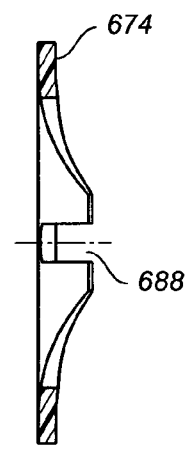
*FIG. 12D*   *FIG. 12E*   *FIG. 12F*

MULTIFUNCTION ADAPTOR FOR AN OPEN-ENDED CATHETER

CROSS-REFERENCE TO RELATED APPLICATIONS

This application is a continuation-in-part of U.S. patent application Ser. No. 10/803,512 entitled "MULTIFUNCTION ADAPTOR FOR AN OPEN-ENDED CATHETER" filed on Mar. 18, 2004, which is incorporated herein by reference in its entirety.

STATEMENT REGARDING FEDERALLY SPONSORED RESEARCH OR DEVELOPMENT

Not applicable.

REFERENCE TO A COMPACT DISK APPENDIX

Not applicable.

BACKGROUND OF THE INVENTION

There are a variety of conditions that require injection of fluids into, or withdrawing fluids from, parts of a body below the surface of the skin of the body. During the procedure, symptomatic gas embolism can occur when undissolved gas (e.g., air, $CO_2$) accumulates in the heart and/or pulmonary arteries. This gas can compromise the circulation of blood through the lungs, causing serious injury or death.

Health Devices May-June 1996; 25(5-6):214-5 reported a case of suspected gas embolism. During a hysteroscopy (performed with a patient under intravenous sedation), the patient gasped for air almost immediately upon uterine insufflation. Based on the clinical signs, the medical staff suspected that the patient's condition was caused by a $CO_2$ embolism that originated in the uterus. However, a follow up investigation revealed that the embolized gas was probably air, not $CO_2$. The air may have been introduced into the patient from the dead space in the tubing set used to connect the insufflator to the hysteroscope. This tubing set was not purged before insufflation began. Health Devices recommended that before delivering a fluid to a patient, one must purge air from tubing sets and instruments. Thus, there is a need for a multifunction adaptor for use with an open-ended catheter wherein the multifunction adaptor can be utilized to connect syringe to the proximal end of the catheter for infusing the catheter with saline or purging air from the catheter.

A subcutaneously tunneled catheter is often selected when a catheter might be required to be implanted within a patient for weeks to months. A subcutaneously tunneled catheter can be implanted or removed in the outpatient setting and has a decreased incidence of infection. The typical procedure for implanting the tunneled catheter is by forward tunneling. However, another method of implanting the tunneled catheter is by reverse tunneling as follows: (a) place the distal end of the catheter within the blood vessel through an entry site; (b) mark an exit locations of a tunnel to be formed in a subcutaneous plane; (c) create the subcutaneous channel from the exit to entry site using a tunneler by pushing the tapered end of the tunneler through the skin; (d) attach the proximal end of the catheter to the tapered end of the tunneler; (e) pull the tunneler with the secured catheter from the entry to the exit site, through the subcutaneous channel, while gently holding the catheter distal to the cuff; and (f) detach the catheter from the tunneler and attach a bifurcation element thereto. During the described reverse tunneling technique, the proximal end of a typical catheter tube is open, permitting the entry of air. If the proximal end is clamped, the catheter cannot be reverse tunneled as described. Therefore, there is a need for a multifunction adaptor for coupling the proximal end of the catheter to a tunneler, while providing protection to the proximal opening of the catheter.

It is common to use an implanted catheter to repeatedly access the vascular system of a patient. A flexible guidewire placed in the vascular system can be used to facilitate placement of the catheter, but its use may prevent capping the catheter to prevent fluid loss from or air entering the vascular system during placement. After catheter placement, it is common to attach a valved cap to the catheter connector(s) to prevent fluid loss from or air entering the catheter and vascular system.

U.S. Pat. No. 6,575,960 (Bleed Back Control Assembly and Method) relates to a Y-valved connector. The 'Y-connector' includes a sealing valve that is normally closed except when accessed with a small diameter tube or wire. The sealing valve does not completely prevent air or fluid leakage, but relies on a second user compressible valve to provide a complete seal. In short, there are several problems with the current valves. The flow path through the valve is restricted due to a restricted cross-sectional area, there is a dead space above or below the valve where blood accumulates, which makes it difficult to clean the valve, and the current valves are not designed for use with a guidewire traversing through the same valve. Also, the current valves cannot be accessed multiple times as they are typically screwed on to the catheter and discarded after use.

Therefore, there is a need for an improved multifunction adaptor, which addresses shortcomings in the current products, reduces the risk of contamination, and permits repeated use thereof.

SUMMARY OF THE INVENTION

The multifunction adaptor of this invention comprises a valve integrated within the passageway in the adaptor. The proximal end of the adaptor is configured to receive or interface with one or more medical instruments. The distal end of the adaptor is configured for temporary or permanent connection to the proximal end of a catheter. The multifunction adaptor is for use with an open-ended catheter, such that the multifunction adaptor provides multiple functionalities. For example, the multifunction adaptor may be configured to support two or more of the following functions: (a) sealing the catheter tube except when being accessed by a syringe or a guidewire, to prevent blood loss or air embolism, (b) attaching to a standard luer fitting such as that of syringe to allow flushing of the catheter with a fluid (e.g., saline, etc.), (c) operating as a tunneler connector, and (d) providing for an "over the guidewire" placement or replacement technique. In addition, it should be appreciated that other advantageous functions may also be provided by the multifunction adaptor of the present invention.

In one variation, a slit valve hub connector comprises a hub connector and a slit valve, wherein the slit valve hub connector is capable of being attached to a catheter tube, and the slit valve seals the catheter tube except when being accessed by an introducer, to prevent blood loss or air embolism.

In another variation, the proximal portion of a catheter tubing is shaped to create a valve, and then integrated within a multifunction adaptor housing. For example, a catheter valve hub connector comprises a hub connector and a catheter tube having a slit valve built-in as an integral part of the catheter tube, wherein the slit valve seals the catheter tube except when being accessed by an introducer, to prevent blood loss or air embolism.

In yet another variation, a valve tubing hub connector comprises a hub connector and a tubing having a slit valve built-in the tubing, wherein the hub connector is capable of being removably attached to a catheter tube, and the slit valve seals the catheter tube except when being accessed by an introducer, to prevent blood loss or air embolism.

In another aspect of the invention, the multifunction adaptor is configured as an extension that can be removably coupled to the proximal end of an open-ended catheter. A valve may be integrated within the lumen of the multifunction adaptor. The proximal portion of the adaptor is configured to receive or interface with one or more medical instruments. For example, the proximal portion of the adaptor lumen may include a tapered surface for receiving the male lure of a syringe. A portion of the adaptor lumen surface may also include a raised surface profile for engaging a tunneler, such that the tunneler can be coupled to the catheter through the multifunction adapter. The valve within the lumen may be configured to allow a guidewire to pass therethrough. In one variation, the distal end of the multifunctional adaptor is configured with a locking interface, and the proximal end of the catheter is configured with a corresponding receiving interface, such that the distal end of the multifunctional adaptor can be secured onto the proximal end of the catheter.

These and other embodiments, features and advantages of the present invention will become more apparent to those skilled in the art when taken with reference to the following more detailed description of the invention in conjunction with the accompanying drawings that are first briefly described.

BRIEF DESCRIPTION OF THE DRAWINGS

In FIG. 11A, the distal tapered end of a tunneler is shown inserted within the compression sleeve.

FIG. 12A illustrates another variation of the detachable multifunction adaptor including a locking disk for engaging the distal tapered end of a tunneler.

FIG. 12B illustrates the distal taper end of a tunneler inserted within the lumen of the multifunction adaptor of FIG. 12A. The tunneler is secured onto the multifunction adaptor by the locking disk.

FIG. 12C illustrates the proximal barbed end of a tunneler inserted within the lumen of the multifunctional adaptor of FIG. 12A. The lumen of the multifunction adaptor is configured with a surface profile for engaging the barb on the tunneler.

FIG. 12D shows a frontal view of the locking disk from FIG. 12A.

FIG. 12E shows a side view of the locking disk of FIG. 12D.

FIG. 12F shows a cross-sectional view of the locking disk of FIG. 12D. The cross-section is taken at A-A as shown in FIG. 12D.

In FIG. 13E the various parts are shown disconnected from each other.

In FIG. 14C, the adaptor/catheter combination is shown implemented over a guidewire.

FIG. 17A illustrates one variation of a clip-ring for placement over the barb portion of a tunneler. In FIG. 17A the clip-ring is shown detached from the tunneler.

DETAILED DESCRIPTION OF THE INVENTION

Figure 1:
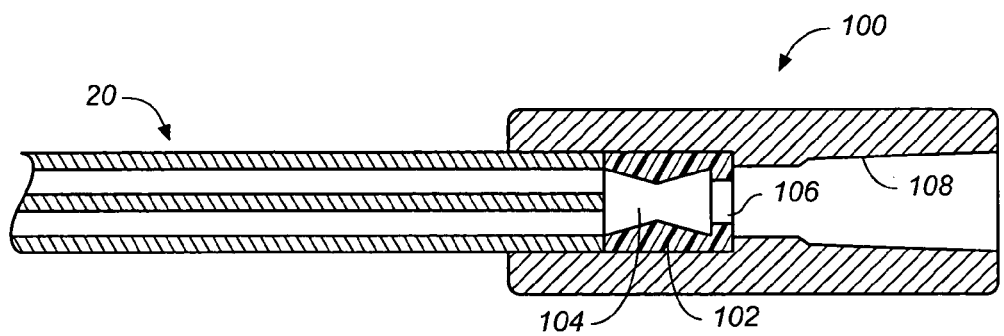
FIG. 1 is a cross-sectional view showing one variation of a slit valve hub connector attached to a proximal end of a catheter.

The following detailed description should be read with reference to the drawings, in which identical reference numbers refer to like elements throughout the different figures. The drawings, which are not necessarily to scale, depict selective embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Before describing the present invention, it is to be understood that unless otherwise indicated this invention need not be limited to applications in humans. As one of ordinary skill in the art would appreciate, variations of the invention may be applied to other mammals as well. Moreover, it should be understood that embodiments of the present invention may be applied in combination with various catheters, tubing introducers or other catheter implantation and connection devices for establishing a fluid conduit into a patient's body.

Reverse tunneling of an implanted dual lumen hemodialysis catheter is used herein as an example application of the multifunction adaptor to illustrate the various aspects of the invention disclosed herein. In light of the disclosure herein, one of ordinary skill in the art would appreciate that variations of the multifunction adaptor may be utilized with various catheters for establishing a fluid conduit into a patient's body. Although the multifunction adaptor may be particularly useful in catheter implantation that requires reverse tunneling, it is contemplated that the multifunction adaptor can also be utilized in various catheter implant procedures, which may not require reverse tunneling, to prevent embolism and/or facilitate over the guidewire placement of the catheter.

It must also be noted that, as used in this specification and the appended claims, the singular forms "a," "an" and "the" include plural referents unless the context clearly dictates otherwise. Thus, for example, the term "a valve" is intended to mean a single valve or a combination of valves, "a fluid" is intended to mean one or more fluids, or a mixture thereof. Furthermore, the words "proximal" and "distal" refer to directions closer to and away from, respectively, a physician operating the device, with the tip end (i.e., distal end) placed inside the patient's body. Thus, for example, the catheter end placed within the body of the patient would be the distal end of the catheter, while the catheter end outside the patient's body would be the proximal end of the catheter.

The multifunction adaptor may be used for facilitating the introduction or removal of fluid to or from a body. The multifunction adaptor may be temporarily attached to a luer fitting connector of a catheter or it may be permanently attached to the catheter in lieu of the luer fitting connection. In one application, the multifunction adaptor is coupled to a catheter which is utilized for chronic excess fluid drainage from a body. In another application, the multifunction adaptor can be coupled to an implantable electromechanically powered and/or magnetically coupled vesicular pump to permit assisted flow of a fluid into or out of a body. This flow may be unidirectional or bidirectional depending on the catheter and the medical procedure.

A multifunction adaptor is attached to the open (proximal) end of a catheter tube (single or multi-lumen, silicone or polyurethane or other suitable polymeric materials). A valve may be integrated within the multifunction adaptor to seal the proximal end of the catheter tubing, except when being accessed by a syringe (for infusion or aspiration), a guidewire, or other medical instruments. One of the applications of the valve is to seal off the open end of the catheter during placement into the vein. This prevents blood loss and/or air embolism that may occur if the catheter's proximal end is open. A second design feature utilizes a multifunction adaptor configured to receive a standard luer interface (i.e., syringe). With a syringe attached to the multifunction adaptor, the catheter may be infused (e.g., flushed with saline, etc.) or aspirated to purge the air within the lumen of the catheter and verify presence of blood/fluid within the catheter lumen. By utilizing the multifunction adaptor, traditional adapters and clamps become unnecessary. A third design feature allows passage of the catheter/multifunction adaptor assembly over a guidewire. The guidewire can be inserted into the catheter tip (distal end) and passed through the guidewire guide in the valve of the multifunction adaptor to direct the guidewire through the valve slit of the valve, and through the multifunction adaptor assembly. Passing the guidewire through the valve minimizes risks associated with blood loss and/or air embolisms possible in an open end catheter design. A fourth design feature allows attachment of the multifunction adaptor to a subcutaneous tunneler directly without any additional attachments or adapters. The multifunctional adaptor may be configured to support one or more of the design features stated above.

In one variation, the multifunction adaptor is configured as a slit valve hub connector as shown in FIG. 1. In one design, the valved hub connector 100 comprises a hard material that has rigidity like that of rigid polyurethane, and includes a first and second ends. The valved hub connector 100 is attached at a distal end thereof to an open proximal end of a catheter tube 20, which can be in single or multiple lumen configurations, and which is generally made of a polymer material, including, but not limited to, silicone and polyurethane. The slit valve hub connector 100 could be attached to the catheter by solvent bonding or by any other method of bonding or overmolding.

In one variation, the valve 102, which is made of silicone or like material, seals the catheter tube except when being accessed by a syringe (for infusion or aspiration) or a guidewire. The valve 102 provides for an "over the guidewire" placement or replacement technique with minimum blood loss or air embolism. A guidewire can be inserted into the distal end of the catheter and passed through a guidewire guide 104 in the valve hub connector 100 to guide the guidewire through the slit 106 of the valve 102 and through the hub connector 100. In one variation, the proximal end of the slit valve hub connector 100, which is not attached to the open end of the attachable catheter tubing, may contain a luer taper 108 as shown in FIG. 1.

The design of the slit opening of the valve may be a single layer slit, a two layer slit, or a triple layer design with a slit followed by a hole opening, followed by another slit opening. The hub connector 100 may be made of a harder material than the valve 102. For example, the hub connector 100 may have a hardness in the range of approximately 90 Shore A to 90 Shore D, while the valve 102 may have a hardness in the range of approximately 40 Shore A to 60 Shore A. However, in one variation, the hub connector has a hardness in the range of approximately 70 Shore A to 80 Shore A.

Figure 2:
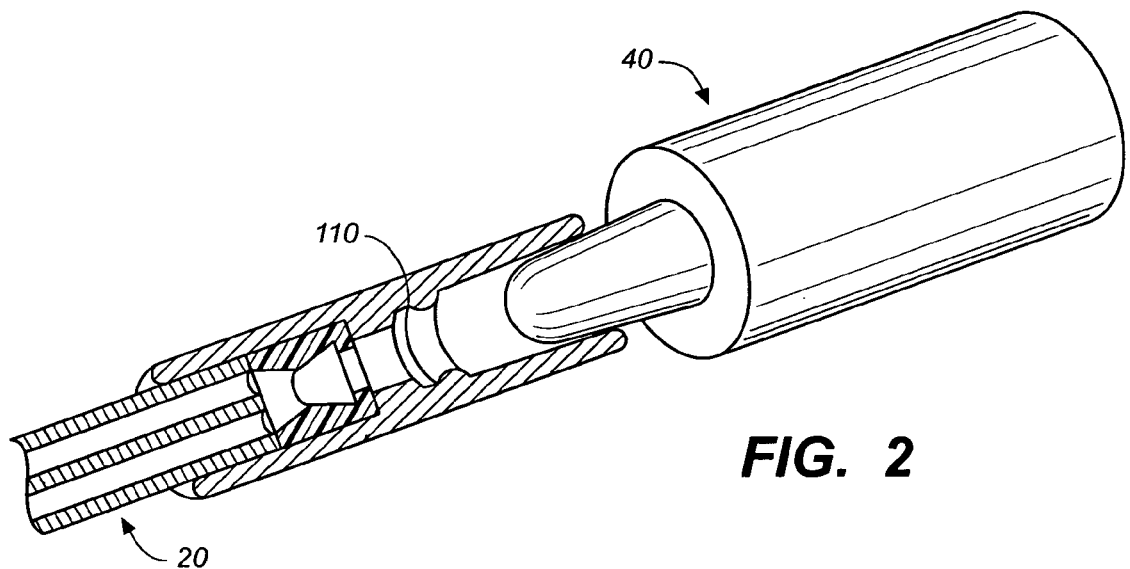
FIG. 2 is a partial cross-sectional view of a syringe connected to the slit valve hub connector of FIG. 1.
Figure 3:
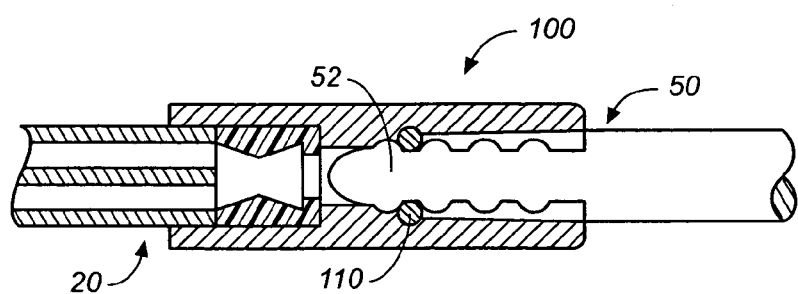
FIG. 3 is a cross-sectional view of a tunneler connected to the slit valve hub connector of FIG. 1.

In the valved connector 100, the proximal end thereof, not attached or connected to the proximal end of an attachable catheter tube, may include a luer taper 108 to receive a standard male luer on a syringe, as shown in FIG. 2. In addition, a snap-on piece, such as an O-ring 110, may also be included in the lumen of the connector for receiving the tip 52 of a tunneler 50, as shown in FIG. 3. While the luer taper and snap-on piece may be particular useful for attachment to certain medical instruments, it should be noted that valved connector 100 may be configured for attachment to, or use with, many different types of medical instruments, including guidewires, syringes and tunnelers, with or without the features on the connectors.

Figure 4A:
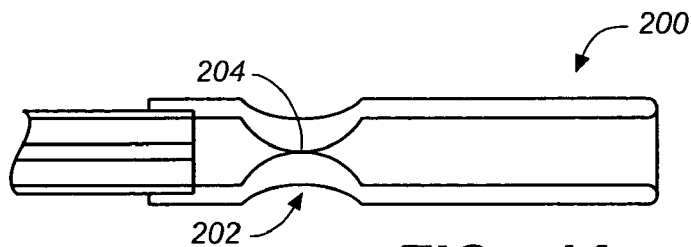
FIG. 4A is a cross-sectional view of another variation of a slit valve hub connector according to the present invention.
Figure 4B:
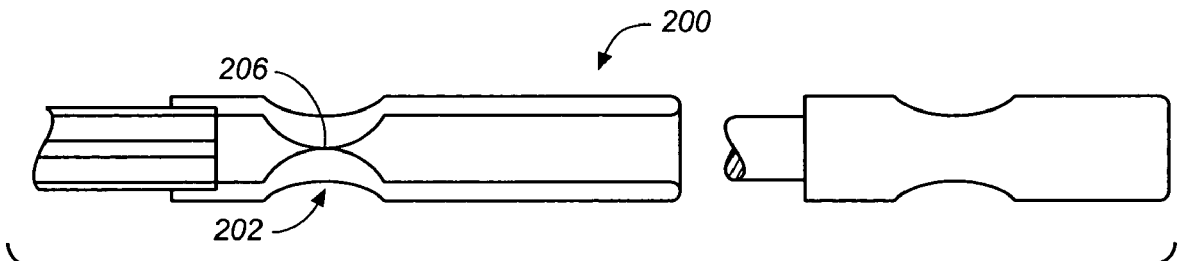
FIG. 4B is a cross-sectional view of yet another variation of a slit valve hub connector.

Another variation of the multifunction adaptor comprises a slit valve hub connector 200 including a built-in slit valve 206, as shown in FIG. 4B. The valved hub connector 200 can be made of a soft material that it has rigidity like that of soft polyurethane (e.g., in the range of approximately 60 Shore A to 90 Shore A). Of course, the hub connector 200 can also be made of a harder material, such as in the range of approximately 80 Shore A to 70 Shore D. There are many ways to manufacture the built-in slit valve 206. For example, as shown in FIG. 4A, one method involves molding the hub connector 200, comprised of a soft material, with a necked portion 202 such that there is initially no opening between the first and second ends as indicated by the solid area 204 therebetween. A slit is subsequently formed through the necked portion to serve as the slit valve 206, as shown in FIG. 4B. In another approach, the housing is configured with a necked portion 202 with an opening therethrough to serve as the hub connector 200.

Figure 4C:
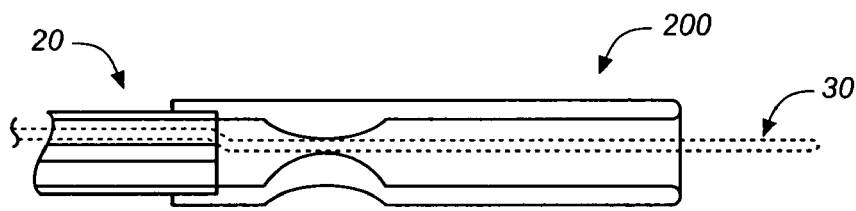
FIG. 4C is a cross-sectional view of the slit valve hub connector with a guidewire passing therethrough.
Figure 4D:
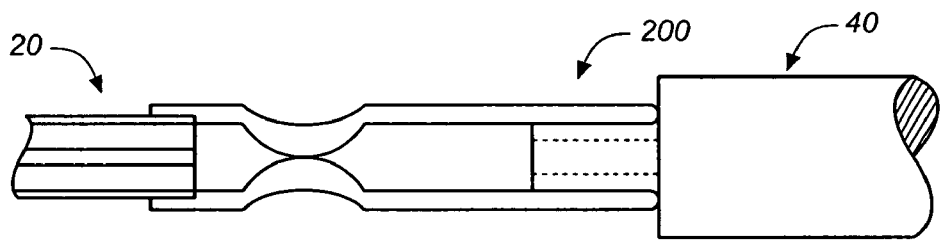
FIG. 4D is a cross-sectional view of a syringe connected to a slit valve hub connector.
Figure 4E:
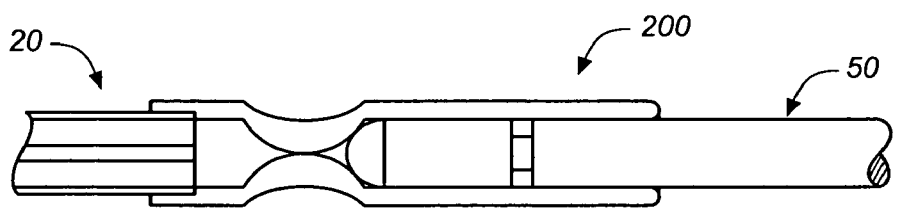
FIG. 4E is a cross-sectional view of a tunneler connected to a slit valve hub connector.

As discussed above, the multifunction adaptor of the present invention can be used to connect to medical instruments to facilitate the use thereof with a catheter. As shown in FIGS. 4C-4E, the valve hub connector 200 can be utilized to allow safe passage of a guidewire 30 through a placed catheter 20 without risk of blood loss or air embolism (FIG. 4C), to connect catheter 20 to a flushing syringe (FIG. 4D), and to connect catheter 20 to a tunneler 50 (FIG. 4E). Of course, the multifunction adaptor of the present invention may be used in conjunction with many other medical instruments as well.

Figure 5A:
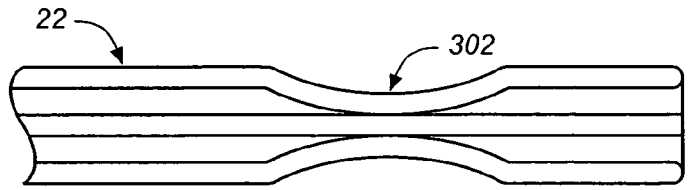
FIG. 5A is a cross-sectional view of a proximal end of a catheter having a valve formed therein.
Figure 5B:
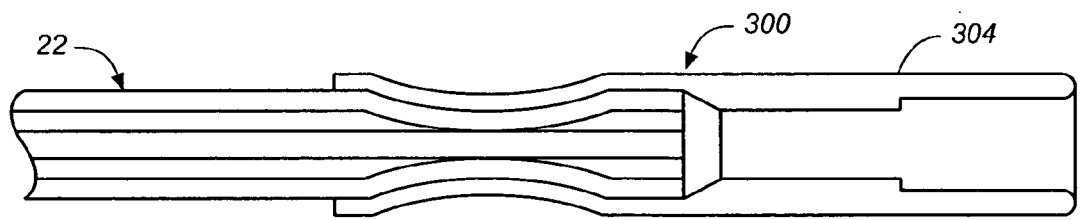
FIG. 5B is a cross-sectional view of the catheter of FIG. 5A with a hub connector overmolded thereon.
Figure 5C:
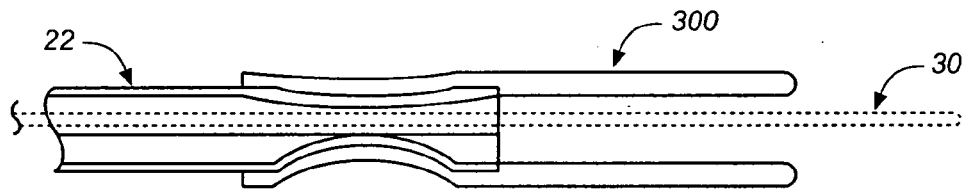
FIG. 5C is a cross-sectional view of the catheter valve hub connector of FIG. 5B with a guidewire passed therethrough.
Figure 5D:
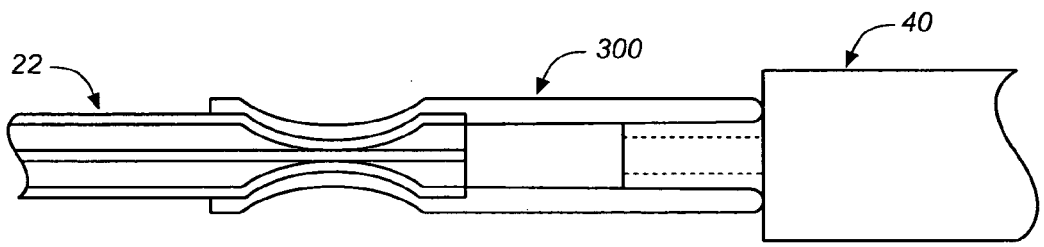
FIG. 5D is a cross-sectional view of a syringe connected to the catheter valve hub connector of FIG. 5B.
Figure 5E:
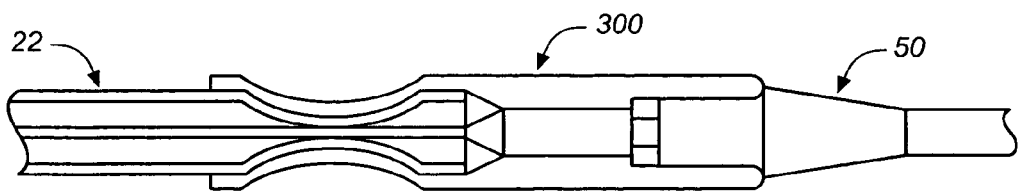
FIG. 5E is a cross-sectional view of a tunneler connected to the catheter valve hub connector of FIG. 5B.

FIGS. 5A-5B illustrate another variation of the multifunction adaptor, the catheter valve hub connector 300. In this variation, a thermoplastic catheter tube 22 is thermoformed to create a valve 302 as shown in FIG. 5A. Over-molded over the valve 302 on the proximal end of the tube 22 is a housing 304, resulting in the hub connector 300. It should be noted that although the catheter tube 22 is shown in a dual-lumen configuration, the valve hub connector 300 is equally applicable to a single or multi-lumen design. The valve 302 seals the catheter tube lumen(s) except when being accessed by a syringe or a guidewire as shown in FIGS. 5C-5D. One of the applications of the valve 302 is to seal off the open end of the catheter during placement into a blood vessel. The valve 302 prevents blood loss or air embolism that may occur in an open ended catheter. As with the embodiments described above, the catheter hub connector 300 permits attachment of a syringe 40 thereto such that the catheter 22 may be infused (e.g., flushed with saline), as shown in FIG. 5D. By utilizing the valved hub connector, traditional adapters and clamps become unnecessary. As shown in FIG. 5E, the catheter hub connector 300 also permits attachment to a subcutaneous tunneler 50 without any additional attachments or adapters.

Figure 6A:
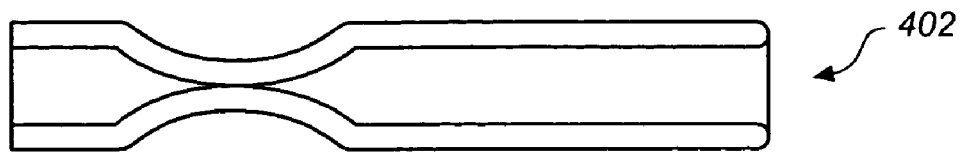
FIG. 6A is a cross-sectional view of a preformed valve tube.
Figure 6B:
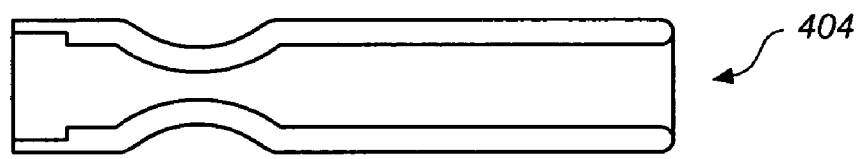
FIG. 6B is a cross-sectional view of a hub connector.
Figure 6C:
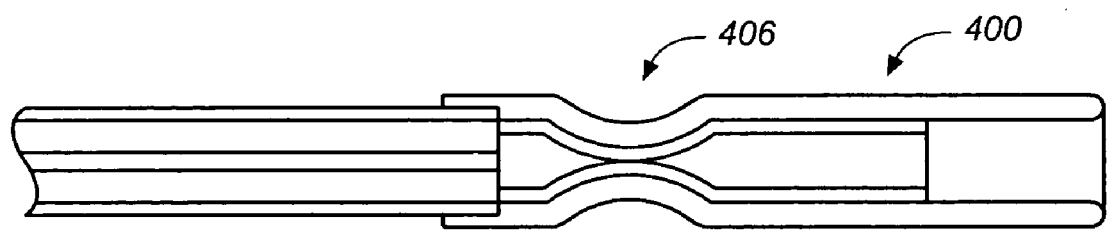
FIG. 6C is a valve tubing hub connector attached to a catheter.

FIG. 6C illustrates yet another variation of the multifunction adaptor of the present invention, valved tubing hub connector 400. The hub connector 400 is manufactured by molding a housing 404 (FIG. 6B) over a preformed valve tube 402 (FIG. 6A). In one example, the housing 404 is made of a hard material (e.g., high durometer silicone), while the valve tube 402 is made of a soft material (e.g., thermoplastic). Examples of the hardness of materials used for the housing 404 is in the range of approximately 60 Shore A to 90 Shore A, while examples for the hardness of the material used for the valve tube 402 is in the range of approximately 40 Shore A to 60 Shore A. The neck portion 406 of the hub connector 400 forms a seal to prevent passage of blood or air therethrough as with the above-described embodiments. The formed hub connector 400 is then attached to catheter 20. In another variation, the valve tube 402 is first formed and placed into a mold adjacent the catheter 20 for over-molding the housing 404. As with the variation described above, hub connector 400 may be used in like manner with medical instruments such as guidewires, syringes and tunnelers.

Figure 7A:
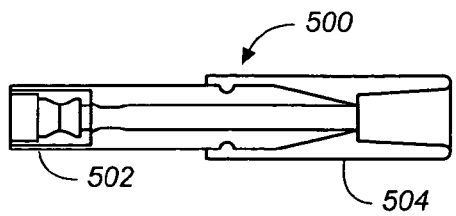
FIG. 7A is a cross-sectional view of another variation of a multifunction adaptor. A removable syringe adaptor is positioned over the proximal end of the multifunction adaptor to configure the multifunction adaptor for receiving a syringe.
Figure 7B:
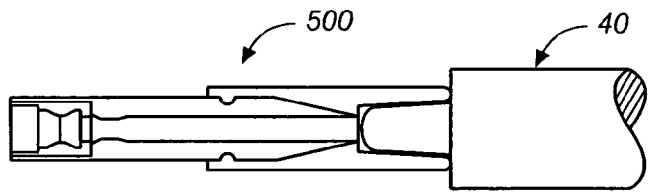
FIG. 7B is a cross-sectional view illustrating the use of a syringe adaptor to couple a syringe to the multifunctional adaptor of FIG. 7A. The syringe is shown inserted into the syringe adaptor in FIG. 7B.
Figure 7C:
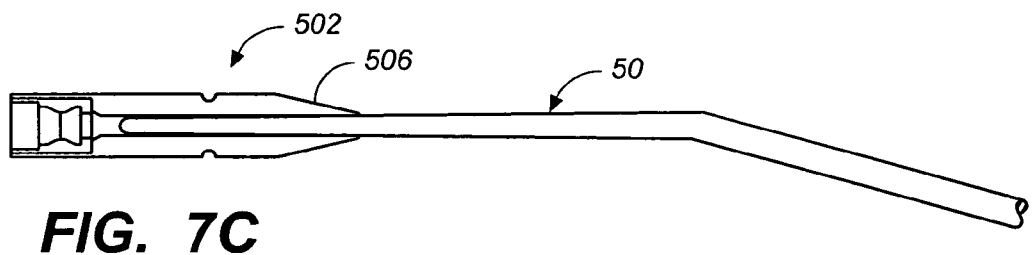
FIG. 7C is a cross-sectional view showing the multifunction adaptor of FIG. 7A with the syringe adaptor removed and the proximal end of a tunneler inserted into the proximal end of the multifunction adaptor.
Figure 7D:
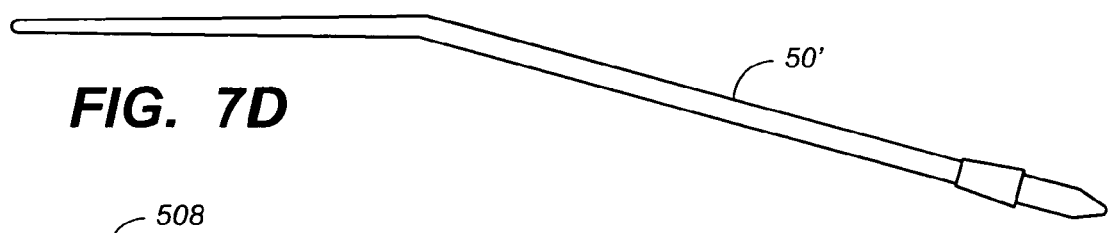
FIG. 7D shows a typical tunneler including a tapered distal end.
Figure 7E:
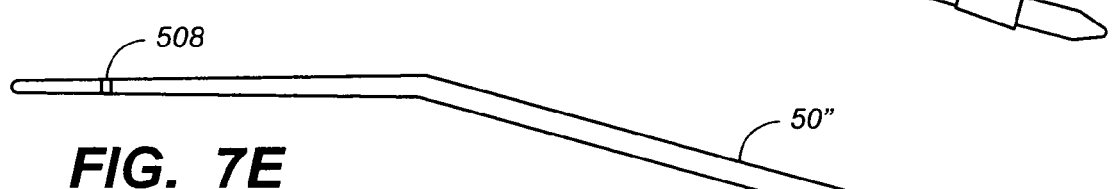
FIG. 7E shows a tapered tunneler with a notch for engaging a protrusion on the inner lumen wall of a multifunction adaptor.
Figure 7F:
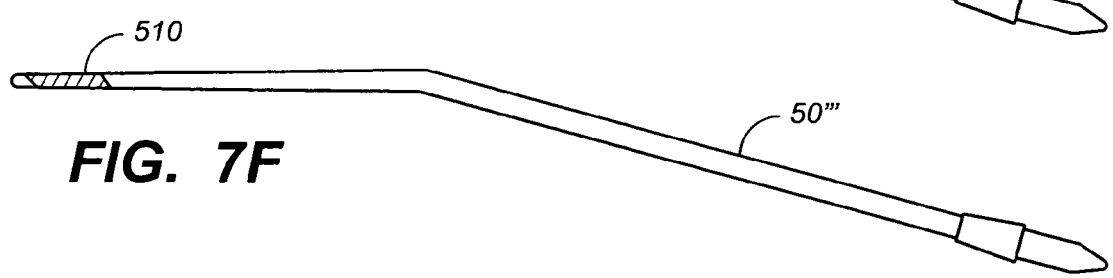
FIG. 7F shows a tapered tunneler with a threaded tip portion for engaging the lumen wall of a multifunction adaptor.

In another variation, a removable syringe adaptor is utilized to establish a fluid connection between a syringe and a connector housing connected to the proximal end of the catheter. In one example, the adaptor assembly 500 comprises a tapered connector housing 502 for receiving a removable syringe adaptor 504, which allows a reverse tunneled catheter to be flushed and attached to the tip of a tunneler 50, as shown in FIGS. 7A-7C. It should be appreciated that the tapered connector housing and removable syringe adaptor can be design features implemented on various adaptors described herein. The adaptor assembly 500 includes a tapered connector housing 502 and a removable syringe adaptor 504. As shown in FIG. 7B, a syringe 40 is attached to the syringe adaptor 504 for flushing a catheter attached to the distal end of the connector housing 502. After flushing, the syringe adaptor is detached and discarded from the connector housing/catheter assembly. After the catheter is inserted into the circulatory system, and the tunneler is positioned in the subcutaneous tunnel, the proximal end of the connector housing 502 is slid over the tip of the tunneler 50. An optional compression mechanism, such as the O-ring 110 illustrated in FIG. 3, or a locking disk, may be provided in the lumen of the connector housing 502, to improve the connector housing's ability to attach to the tunneler. With the tunneler 50 connected to the connector housing 502, the user can then pull the proximal portion of the catheter through the subcutaneous tunnel and exit at the exit site. The connector housing outside diameter creates the desired subcutaneous tunnel diameter while the tapered tip 506 eases the connector/catheter passage. In one variation, the connector housing is configured for use with a standard tunneler 50' (FIG. 7D), a tunneler 50" with a locking notch 508 (FIG. 7E), or a tunneler 50''' with shallow threads 510 at the tip (FIG. 7F) to allow the tunneler to be removed (unthreaded) from the connector housing.

Variations of the multifunction adapter may be designed to be small enough to fit within a cylindrical housing with maximum dimensions of about 0.5" diameter and 1.0" length. The multifunction adapter may also be designed to be incorporated within a small housing that is compatible with multiple fittings (e.g., luer lock, slip fit, compression, etc.). Valve function or performance is not affected by the addition of color or clear housing/components. Component or housing components are not affected by opacity or color. Markings and scales may be used on an as needed basis per application. Device function is not integrally linked to markings, etc. In one variation, the multifunction adapter comprises of materials that are sterilizable using standard techniques (e.g., EtO, gamma, etc.). The methods of manufacturing the multifunction adapter of the different variations include machining or molding the components of the valved tubing and hub connector.

Figure 8:
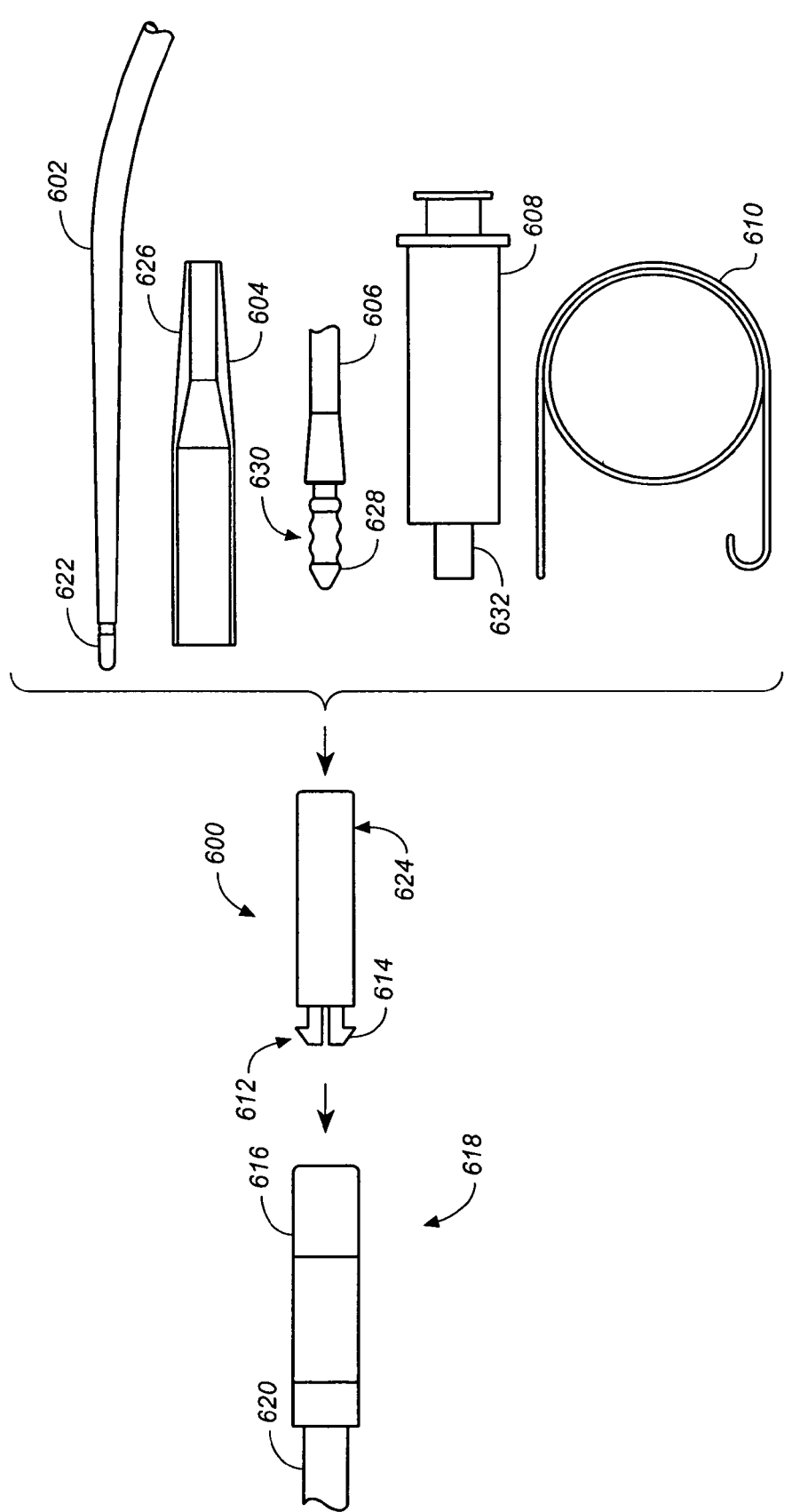
FIG. 8 illustrates one variation of a detachable multifunction adaptor. The distal end of the multifunction adaptor is configured for coupling to the proximal end of a catheter. The proximal end and the lumen of the multifunction adaptor are configured to receive one or more of the medical instruments shown on the right side of FIG. 8. The medical instruments shown, from top to bottom, are: the tapered end of a tunneler; an oversleeve adaptor for use with a tunneler; the proximal barbed end of a tunneler; a syringe; and a guidewire.

In another aspect of the invention, the multifunction adaptor is configured such that it can be removably attached to the proximal end of a catheter and also serve as an interface/conduit for implementing additional medical instruments on/with the catheter. As shown in FIG. 8, the detachable multifunction adaptor 600 may be configured to support one or more instruments from a group of medical instruments 602, 604, 606, 608, 610 shown on the right side of FIG. 8. In one variation, the multifunction adaptor 600 is configured to support all five pieces 602, 604, 606, 608, 610 of the medical instruments shown in FIG. 8. The distal end 612 of the multifunction adaptor 600 is configured with a locking mechanism 614 for engaging the hub 616 attached to the proximal end 618 of the catheter 620. The user inserts the locking mechanism 614 into the lumen/passageway of the catheter hub 616 to attach the multifunction adaptor 600 to the catheter 620. In one design, the user simply applies a force in the proximal direction to pull the multifunction adaptor 600 off of the catheter hub 616. In another design, a latch may be provided to secure the multifunction adaptor on the catheter hub, such that the latch must be depressed/disengaged before the multifunction adaptor can be removed. In yet another design, a tool is required to disengage the latch in order to remove the multifunction adaptor, such that accidental removal of the multifunction adaptor is prevented. With the multifunction adaptor attached to the hub on the catheter, a valve integrated within the multifunction adaptor seals the proximal opening of the catheter and at the same time allows various medical instruments to access the catheter.

Once that multifunction adaptor 600 is connected to the catheter 620, the user can insert the distal tapered end 622 of the tunneler 602 into the proximal lumen of the multifunction adaptor 600. The multifunction adaptor 600 grips onto the tunneler 602 and allows the user to drag the catheter 620 by pulling on the tunneler 602. The oversleeve 604 may be placed over the proximal end 624 of the multifunction adaptor 600 prior to insertion of the distal tapered end 622 of the tunneler 602. The oversleeve 604 provides a tapered profile 626 between the tunneler 602 and the multifunction adaptor 600 interface, such that the multifunction adaptor along with the catheter can be easily pulled through a subcutaneous tunnel. The oversleeve 604 may also help center and/or secure the tunneler on the multifunction adaptor.

The multifunction adaptor 600 can also be configured with a large enough lumen opening at the proximal end 624 to receive and secure onto the proximal end 628 of a tunneler 606. Within the lumen of the multifunction adaptor 600, a surface profile and/or a locking interface may be provided to grip onto the barbs 630 at the proximal end 628 of the tunneler 606. In addition, the proximal portion of the adaptor lumen may be provided with a tapered surface for receiving the male luer 632 on a syringe 608, such that the user may connect a syringe 608 or a fluid/suction source onto the adaptor to deliver and/or remove fluids from the lumen of the catheter 620. Furthermore, the catheter/multifunction adaptor combination may be inserted over a guidewire 610 and advanced into the patient's circulatory system. The valve in the multifunction adaptor can maintain a seal around the guidewire while the catheter/multifunction adaptor unit is displaced in relation to the guidewire.

In one exemplary application for implanting a catheter 620, the user first places a guidewire 610 into the patient's circulatory system and positions the guidewire for the introduction of a catheter using methods that are well known to one of ordinary skill in the art. The user then attaches the multifunction adaptor 600 onto the proximal end 618 of the catheter 620. A fluid may be injected into the catheter through the multifunction adaptor 600 to purge the air within the lumen of the catheter 620 prior to insertion of the catheter. A syringe 608 filled with saline or other appropriate fluid may be inserted into the proximal end 624 of the multifunction adaptor 600 to inject fluid into the catheter 620. The distal end of the catheter is then inserted over the proximal end of the guidewire and advanced into the patient's circulatory system. Eventually, the proximal end of the guidewire 610 will pass through the valve in the multifunction adaptor 600 and exit the proximal opening on the multifunction adaptor. Once the catheter is in place, the guidewire 610 can be removed. As the guidewire is pulled out through the proximal opening of the multifunction adaptor, the valve within the multifunction adaptor prevents blood from spilling out of the proximal end of the catheter.

If reverse tunneling of the implanted catheter is desirable, the user can then insert a tunneler 602 through a pre-cut subcutaneous channel, and then attach the proximal end 624 of the multifunction adaptor 600 to the tip of the tunneler 602 that has passed through the subcutaneous channel. Once the catheter 620 is coupled to the tunneler 602 through the multifunction adaptor 600, the user can pull a proximal portion of the implanted catheter 620 through the subcutaneous channel. With the proximal portion of the catheter outside the exit site of the subcutaneous channel, the user can remove the tunneler 602 by disconnecting the multifunction adaptor 600 from the catheter 620. Once the adaptor 600 is removed, the user may then connect extension tubing (e.g., extension catheter, bifurcation catheter, etc.) onto the proximal end 618 of the catheter 620. In certain applications, it may be desirable to maintain the seal at the proximal end of the catheter 620 by keeping the multifunction adaptor 600 on the catheter 620 and simply disconnecting the tunneler 602 from the multifunction adaptor 600.

One of ordinary skill in the art having the benefit of this disclosure would appreciate that the user may use a syringe 608 along with the multifunction adaptor 600 to purge trapped air from the lumen of the catheter before and/or after tunneling of the catheter. With the multifunction adaptor 600 connected to the catheter 620, the user may also pre-fill the lumen of the catheter 620 with saline prior to inserting the catheter 620 into the patient's body. The multifunction adaptor 600 disclosed herein may be configured for utilization with various medical instruments, including, but not limited to, the instruments shown in FIG. 8.

Figure 9A:
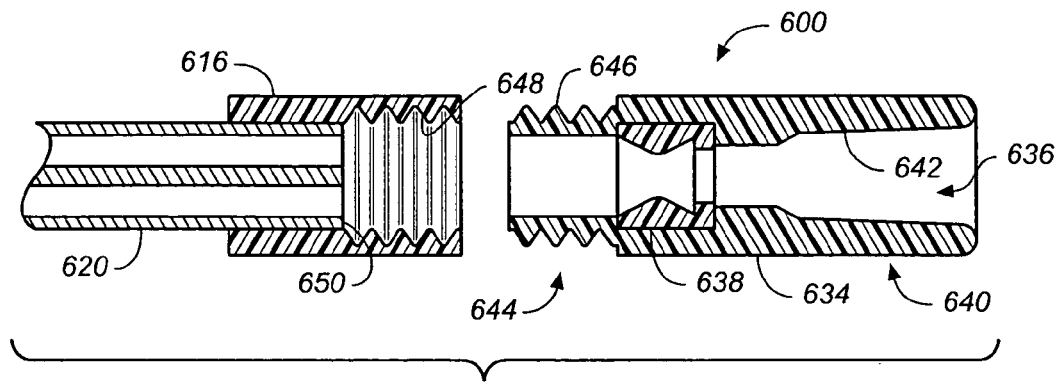
FIG. 9A is a cross-sectional view illustrating another variation of a detachable multifunctional adaptor including a coupling surface which comprises a plurality of groves. The proximal end of the catheter comprises a connector hub/housing with corresponding groves for receiving the detachable multifunction adaptor.
Figure 9B:
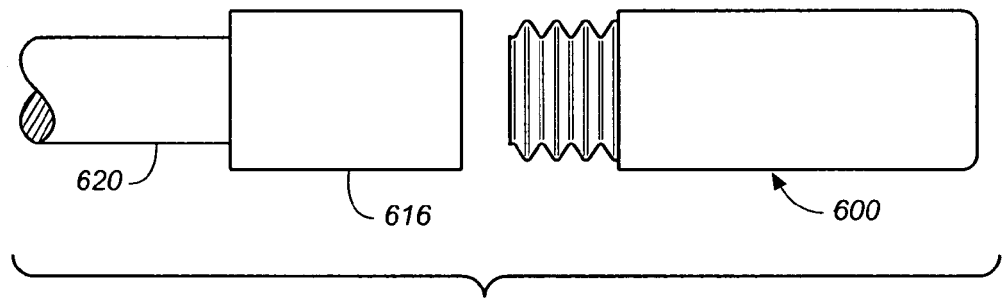
FIG. 9B is a plain view of the detachable multifunction adaptor and its corresponding catheter from FIG. 9A.
Figure 9C:
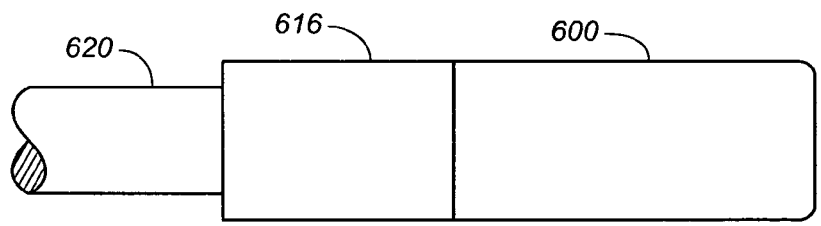
FIG. 9C illustrate the detachable multifunction adaptor of FIG. 9A connected to its corresponding catheter.

Referring to FIG. 9A, one variation of a multifunction adaptor 600 is illustrated. The multifunction adaptor 600 comprises a housing 634 with a passageway 636 (e.g., lumen, etc.). A valve 638 is positioned within the passageway 636 of the adaptor 600. The proximal portion 640 of the passageway 636 is tapered 642 for receiving a male luer. The distal end 644 of the housing 634 is configured with grooves 646 for interfacing with a corresponding surface 648 within the connector hub 616, which is attached to the proximal end 650 of the catheter 620. The grooves may comprise a polymeric material such that the multifunction adaptor can be snapped into the connector hub on the catheter. In another variation, the distal end 644 of the multifunction adaptor is configured with male threads, while the inner lumen surface 648 of the connector hub 616 is configured with corresponding female threads, such that the multifunction adaptor 600 can be screwed onto the proximal end of the catheter 620. FIG. 9B shows the multifunction adaptor 600 disconnected from the catheter 620 and FIG. 9C shows the multifunction adaptor 600 connected to the catheter 620.

Figure 10:
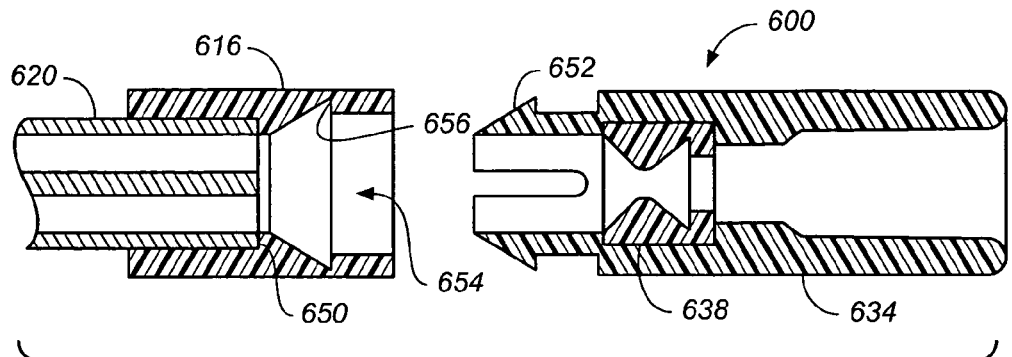
FIG. 10 illustrates another variation of a detachable multifunction adaptor with a barb-shaped locking interface on the distal end of the adaptor. A hub attached to the proximal end of the catheter includes a notch for receiving the barb-shaped locking interface. In this variation the detachable multifunction adaptor includes an integrated valve within the passageway of the adaptor housing.

FIG. 10 illustrates another variation, where the multifunction adaptor 600 is configured with a barb-shaped locking interface 652 at the distal end 644 of the adaptor housing 634. A connector hub 616 is provided at the proximal end 650 of the catheter 620 to receive the multifunction adaptor. The lumen 654 of connector hub 616 is configured with a notch 656 for engaging the barb shaped locking interface 652 on the multifunction adaptor 600. In this example, the barb portion 652 of the housing 634 can be compressed toward a longitudinal axis of the housing, such that the user can snap the barb-shaped locking interface 652 into and out of the connector hub 616.

Figure 11A:
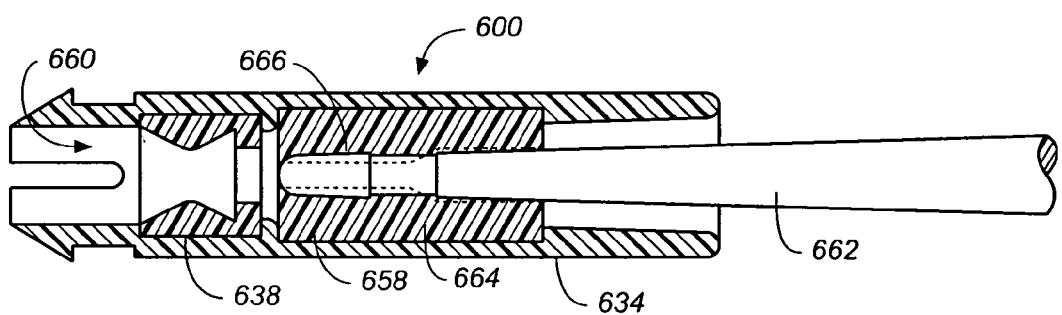
FIG. 11A illustrates another variation of a detachable multifunction adaptor including a compression sleeve for engaging a tunneler.
Figure 11B:
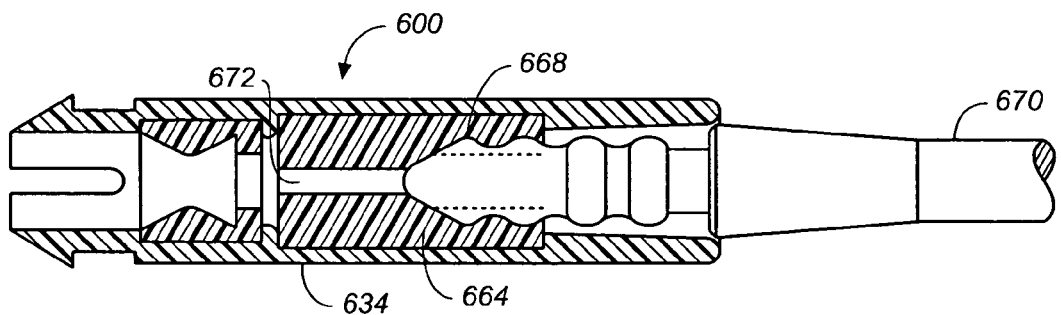
FIG. 11B illustrate the detachable multifunction adaptor of FIG. 11A with the proximal barbed end of a tunneler inserted within the compression sleeve.

The multifunction adaptor 600 may further comprise a compression mechanism 658 positioned within the lumen 660 of the adaptor housing 634 for securing a tunneler 662 to the multifunction adaptor 600. In one variation, as shown in FIG. 11A, a compression sleeve 664 is placed within the housing 634 to capture the tip 666 of the tunneler 662. The compression sleeve 664 may be configured with a pliable material and a large enough lumen to accommodate both the distal tapered tip and the proximal barbed end of a tunneler. The compression sleeve may be comprised of silicone, plastic, or various other polymeric materials. FIG. 11A illustrates the distal tapered tip 666 of a tunneler 662 inserted within the compression sleeve 664. The lumen of the compression sleeve expands around the tip 666 of the tunneler and grips onto the tunneler 662. FIG. 11B illustrates another application, where the proximal barbed end 668 of a tunneler 690 is inserted within the compression sleeve 664. The lumen 672 of the pliable compression sleeve 664 expands to accommodate the barb 668, and the compression force from the sleeve 664 couples the tunneler 670 to the multifunction adaptor 600.

FIG. 12A illustrates another variation where a compression mechanism, which comprises a locking disk 674, is positioned within the lumen 660 of the multifunction adaptor 600. The multifunction adaptor 600 is configured with a polymeric valve 676, which includes a slit opening 678 at the proximal end 680 and an hourglass-shaped lumen 682. The proximal portion 684 of the adaptor lumen is configured to receive a male luer. A section of the adaptor lumen wall comprises a raised surface profile 686 for engaging the barb on the proximal end of a tunneler. In this variation, the locking disk 674, as shown in FIG. 12D, has a center opening 688 for receiving the distal tapered tip 690 of a tunneler 692. FIG. 12B shows the distal tip 690 of the tunneler 692 inserted into the lumen 660 of the multifunction adaptor 600, engaging the locking disk 674. FIG. 12C shows the proximal barbed end 694 of a tunneler 696 inserted into the lumen 660 of the multifunction adaptor 600. The barb on the tunneler engages the raised surface profile 686 on the inner wall of the adaptor lumen 660. FIG. 12E shows a side view of the locking disk 674, and FIG. 12F shows a cross-sectional view of the locking disk 674. One of ordinary skill in the art having the benefit of this disclosure would appreciate that various other compression mechanisms or locking interfaces may also be implemented within the multifunction adaptor to secure a tunneler that is inserted therein.

Figure 13A:
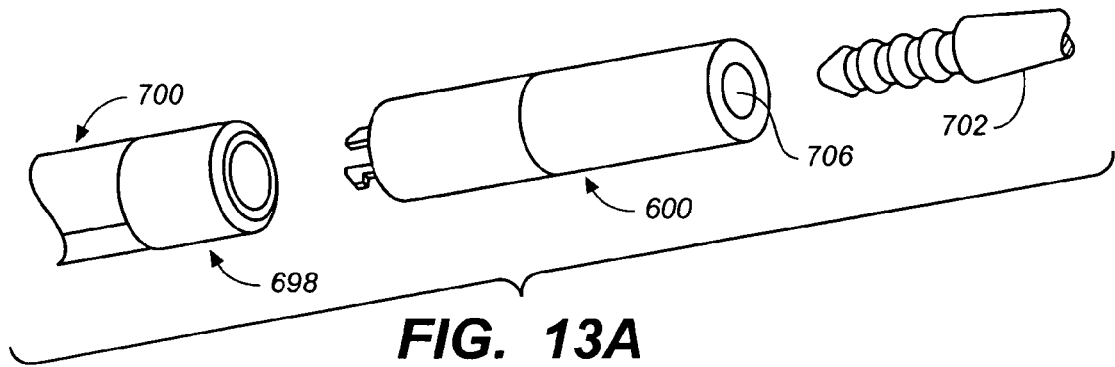
FIG. 13A illustrates one possible application of the detachable multifunction adaptor of FIG. 12A. The multifunction adaptor is position to couple the proximal end of a catheter to a tunneler. The tunneler, the multifunction adaptor, and the catheter are shown detached form each other.
Figure 13B:
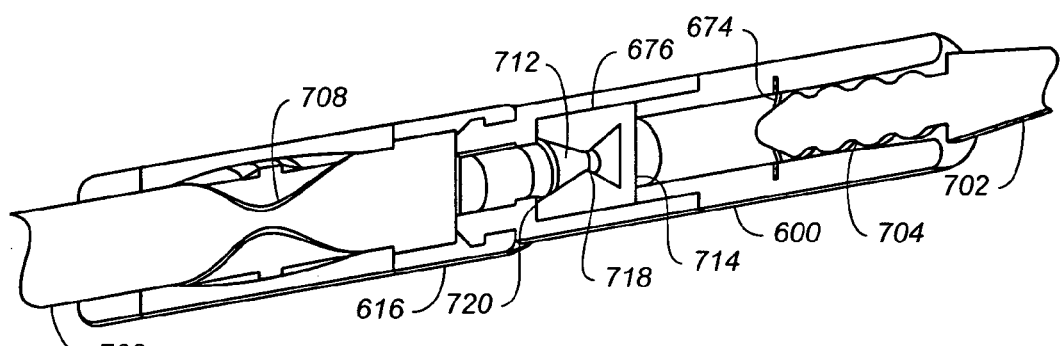
FIG. 13B is a cross-sectional view illustrating the catheter, the multifunction adaptor, and the tunneler from FIG. 13A inter-connected to each other.

FIG. 13A illustrates the multifunction adaptor 600 from FIG. 12A being utilized for coupling the proximal end 698 of a catheter 700 to a tunneler 702. In FIG. 13A, the catheter 700, the multifunction adaptor 600, and the tunneler 702 are shown detached from each other. FIG. 13B is a cross-sectional view showing the multifunction adaptor 600 inserted within the connector hub 616 at the proximal end 698 of the catheter 700, and the barbed end 704 of the tunneler inserted within the proximal opening 706 of the multifunction adaptor 600. In this particular example, a dual lumen catheter 700, including a built-in slit valve 708, is implemented with the multifunction adaptor 600. One of ordinary skill in the art having the benefit of this disclosure would appreciate that the design shown in FIG. 13B can also be utilized with a catheter having one, three or more lumens. The catheter may have its own built-in valve, or a catheter without an integrated valve may be utilized. U.S. patent application Ser. No. 10/803,207 entitled "VALVED CATHETER" filed Mar. 18, 2004, which discloses a catheter with an integrated valve, is hereby incorporated by reference in its entirety.

Figure 13C:
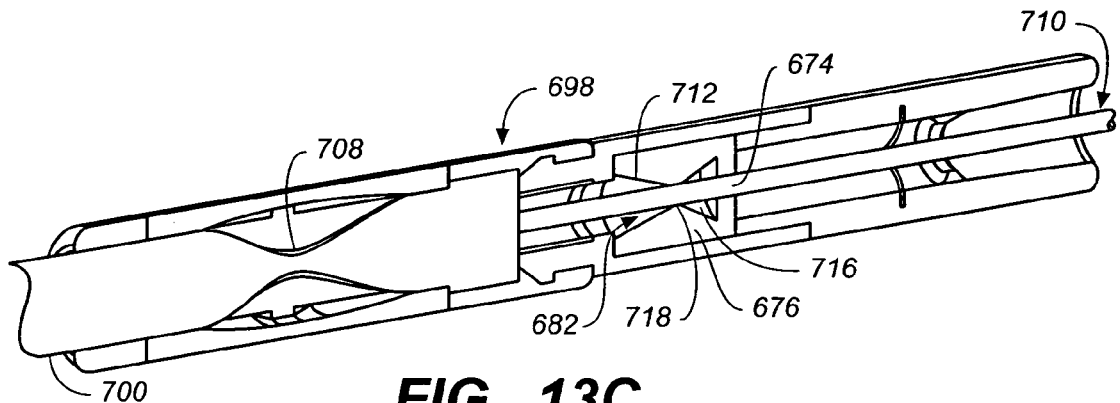
FIG. 13C illustrates the use of the multifunction adaptor of FIG. 12A to provide proximal end protection for an over the guidewire placement of a catheter.

FIG. 13C illustrates the multifunction adaptor 600 of FIG. 12A being utilized with a catheter 700 for over-the-guidewire placement of the catheter 700. As the distal end of the catheter 700 is inserted over the proximal end of the guidewire 710 and advanced into the body of the patient, the proximal end of the guidewire 710 is displaced with respect to the lumen of the catheter 700. Eventually the proximal end of the guidewire 710 enters the multifunction adaptor 600, which is attached to the proximal end 698 of the catheter 700. As shown in FIG. 13C, the valve 676 with an hourglass lumen 682 may be particularly useful in this application. Because a dual lumen catheter 700 is used in this example, the guidewire 710 is offset from the central axis of the catheter 700. The distal cone-shaped profile 712 of the hourglass lumen centers the proximal end of the guidewire as the guidewire is displaced/advanced into the valve 676 structure.

Figure 13D:
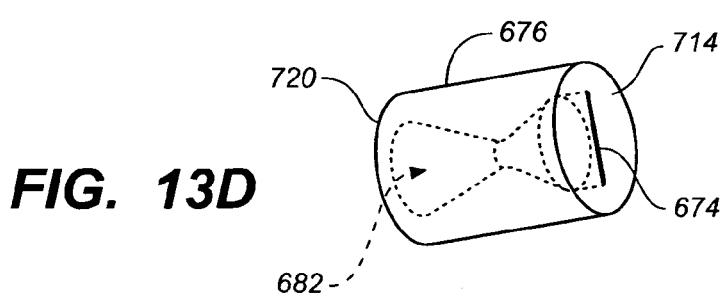
FIG. 13D shows the valve implemented within the lumen of the multifunction adaptor of FIG. 12A.

The centering of the guidewire 710 ensures the guidewire passes through a center portion of the valve slit 674. This allows the guidewire 710 to pass-through smoothly, and prevents it from damaging the valve slit 674. In this example, the valve 676, illustrated in FIG. 13D, comprises a cylindrical shaped polymeric body including an hourglass-shaped lumen 682, and a slit opening 674 on the proximal end 714 to allow fluids and objects to pass through. The cavity 716 forming the proximal portion of the hourglass lumen 682 allows the valve slit 674 to open both inwardly and outwardly. The neck portion of the lumen forms the 'guidewire guide' 718 to center the guidewire 710 in relation to the valve slit 674. The cone-shaped distal portion 712 of the valve lumen may prevent the guidewire 710 from getting caught-up or "hanging" at the distal side 720 of the valve, and helps direct the guidewire 710 through the valve structure 676. As one of ordinary skill in the art having the benefit of this disclosure would appreciate, the multifunction adaptor with an hourglass valve may also be utilized with a single lumen catheter. In applications where a catheter with a larger diameter is utilized, the guidewire may lay against one side of the catheter wall as it is displaced within the lumen of the catheter. The hourglass valve can re-center the guidewire before it is inserted through the valve slit.

Furthermore, the neck portion of the valve 676 may also be configured to serve as a sealing surface around an advancing guidewire, such that the proximally advancing guidewire is sealed prior to advancing and opening the valve slit 674 at the proximal end of the valve structure 676. This design may prevent air from entering into the catheter, or blood from exiting the out of the catheter through the valve slit 674, when the catheter is inserted into the patient through over-the-guidewire placement. In one variation, the guidewire guide 718, which is located within the valve 676, is configured with an inner circumferential surface about the size of the outer diameter of the guidewire 710. As the guidewire 710 is inserted through the guidewire guide 718, the guide-wire guide 718 seals around the catheter and prevents fluid from flowing pass the neck of the valve in either direction. This design may allow a seal to be established within the valve structure 676 before the proximal end of the guidewire is displaced in the proximal direction to force the valve slit 674 to open up and permit the guidewire 710 to pass through.

Figure 13E:
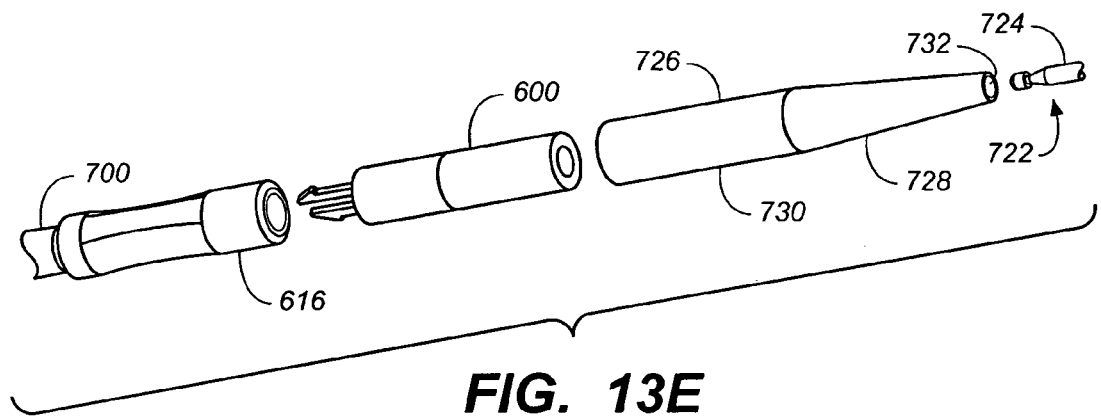
FIG. 13E illustrates the used of an oversleeve, which is to be positioned over the proximal end of the multifunction adaptor, to connect the distal tapered end of a tunneler to the multifunction adaptor.
Figure 13F:
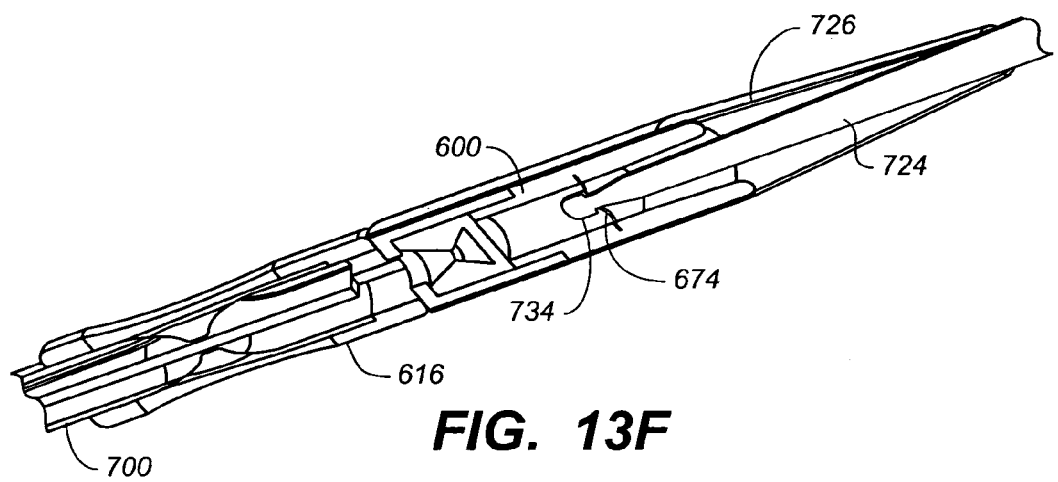
FIG. 13F is a cross-sectional view showing the various parts from FIG. 13E coupled to each other.

FIG. 13E illustrates the use of the multifunction adaptor 600 of FIG. 12A to couple the distal tapered end 722 of a tunneler 724 to a catheter 700. As shown in the example of FIG. 13E, an oversleeve 726 is provided to center the tunneler 724 and to provide a smooth surface profile between the tunneler/multifunction adaptor interface. The tapered circumferential surface 728 of the oversleeve 726 may assist the user in pulling the assembly through a small diameter subcutaneous channel. As the oversleeve is pulled through the subcutaneous channel, the distal (expanded) portion 730 of the oversleeve 726 may force the subcutaneous tunnel to expand, thus facilitating the pass-through of the catheter 700. The user may first insert the multifunction adaptor 600 into the hub 616 at the proximal end of the catheter 700. The oversleeve 726 may then be placed over the multifunction adaptor 600. The distal tip 734 of the tunneler 724 is inserted into the proximal opening 732 of the oversleeve 726 and then advanced into the multifunction adaptor 600 to engage the locking disk 674 within the multifunction adaptor 600, as shown in FIG. 13F.

Figure 14A:
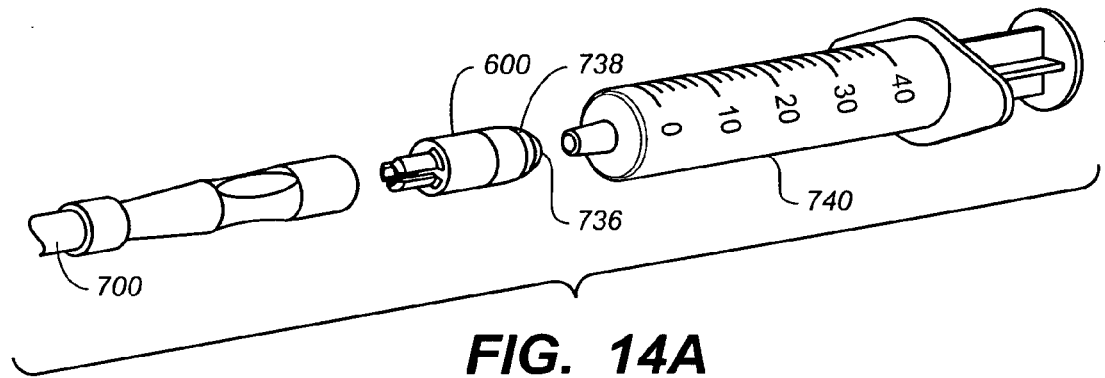
FIG. 14A illustrates another variation of a detachable multifunction adaptor along with its corresponding catheter, which includes a connector hub. The adaptor is shown with a syringe including a male luer for insertion into the distal end of the multifunction adapter.
Figure 14B:
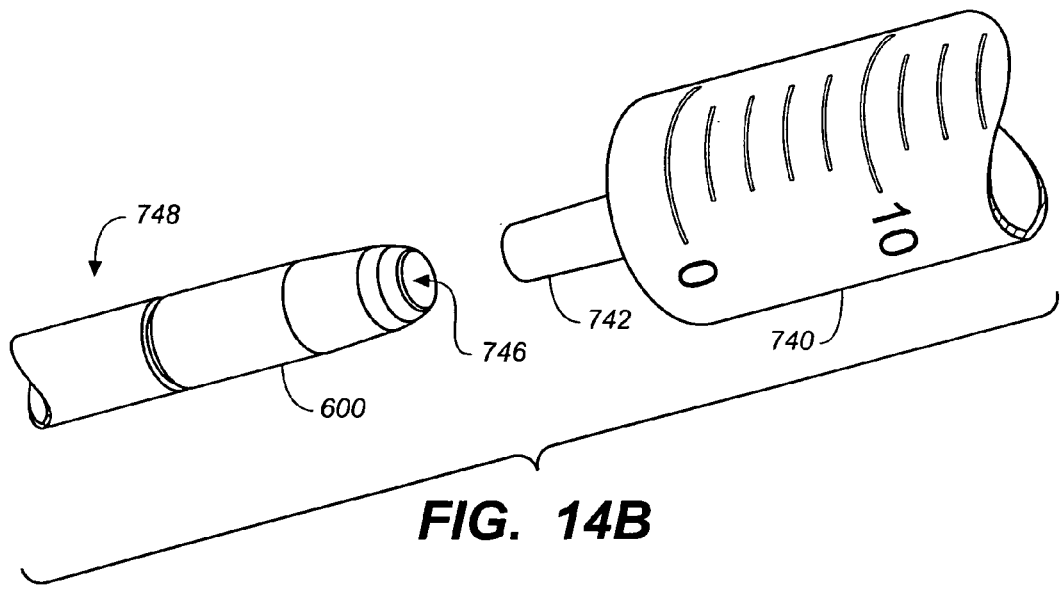
FIG. 14B illustrates the detachable multifunction adaptor of FIG. 14A attached to the proximal end of the catheter.

FIG. 14A shows another variation of a multifunction adaptor 600. In this variation, the proximal end 736 of the multifunction adaptor 600 includes a tapered/bullet-shaped surface profile 738. The multifunction adaptor 600 is shown detached from the catheter 700. A syringe 740 that can be inserted into the proximal end 736 of the multifunction adaptor 600 is also shown in FIG. 14A. FIG. 14B shows the multifunction adaptor 600 coupled to the proximal end 748 of the catheter, and ready to receive the male luer interface 742 on the syringe 740. The proximal portion of the adaptor lumen 746 is configured with a tapered profile, which matches the male luer 742.

Figure 14C:
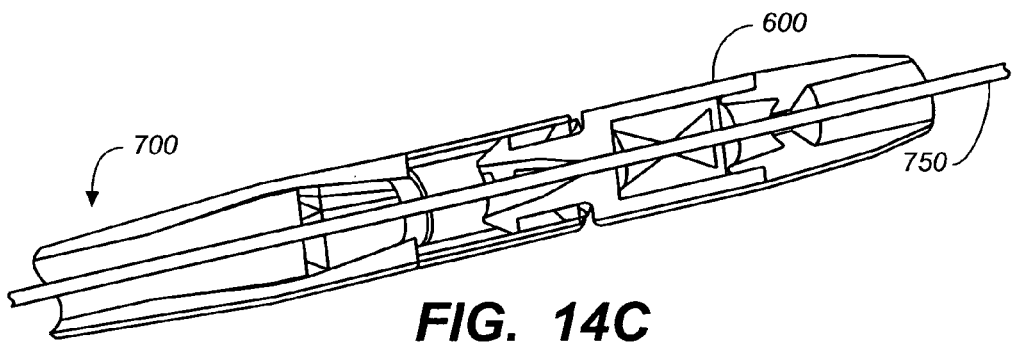
FIG. 14C is a cross-sectional view showing the multifunction adaptor of FIG. 14A attached to the proximal end of the catheter.
Figure 14D:
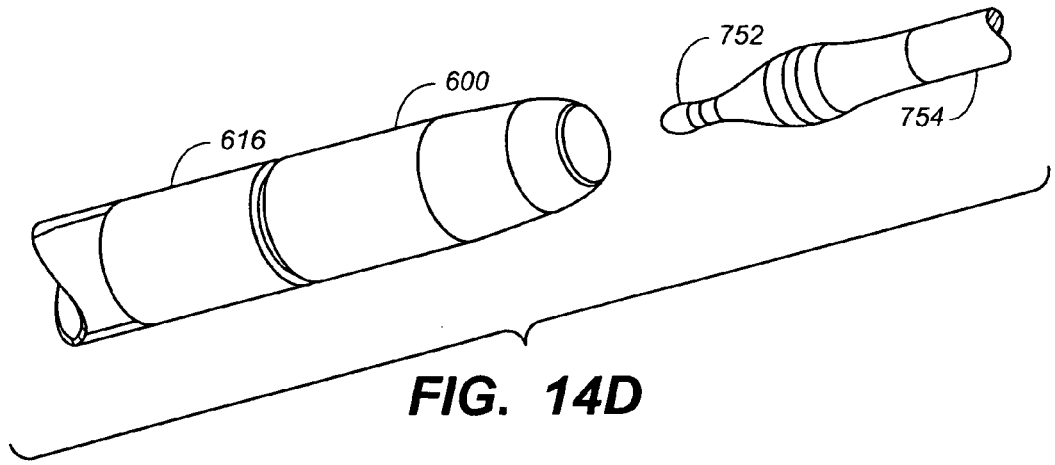
FIG. 14D illustrates the adaptor/catheter combination of FIG. 14B positioned to receive the barbed end of a tunneler.
Figure 14E:
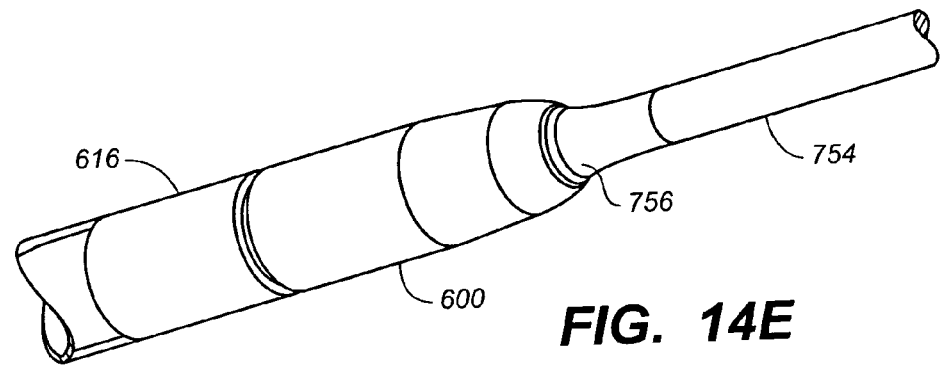
FIG. 14E illustrates the tunneler of FIG. 14D inserted into the multifunction adaptor.
Figure 14F:
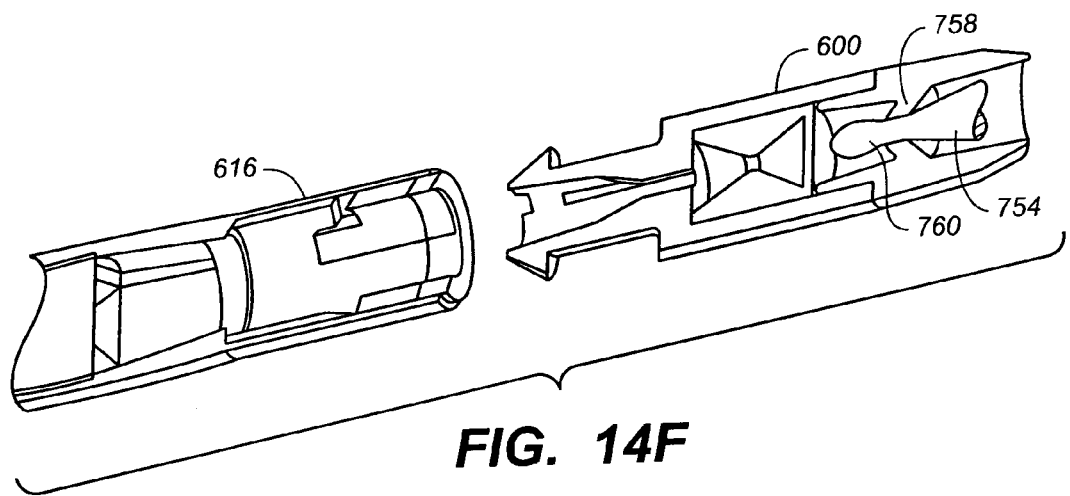
FIG. 14F is a cross-sectional view illustrating the detachment of the multifunction adaptor of FIG. 14E form its corresponding catheter while the adaptor is still attached to the tunneler.

FIG. 14C shows the multifunction adaptor 600 and catheter 700 combination being implemented over a guidewire 750. FIG. 14D shows the barbed end 752 of a tunneler 754 positioned for insertion into the multifunction adaptor 600. FIG. 14E shows the tunneler 754 of FIG. 14D inserted into the multifunction adaptor 600. The proximal portion of the multifunction adaptor is configured such that its rounded profile 738 blends into the outer circumferential surface 756 of the tunneler's shaft. The smooth surface transition may minimize friction as the multifunction adaptor 600, along with the catheter, is pulled into the subcutaneous channel. Once the proximal portion of the catheter is tunneled through the subcutaneous channel, the user may remove the multifunction adaptor 600 along with the attached tunneler 754, as shown in FIG. 14F. FIG. 14F also illustrates the locking interface 758 that engages the barb 760 at the tip of the tunneler 754. The locking interface 758 secures the tunneler 754 and allows the user to exert force through the multifunction adaptor and draw the attached catheter through the subcutaneous channel.

Figure 15:
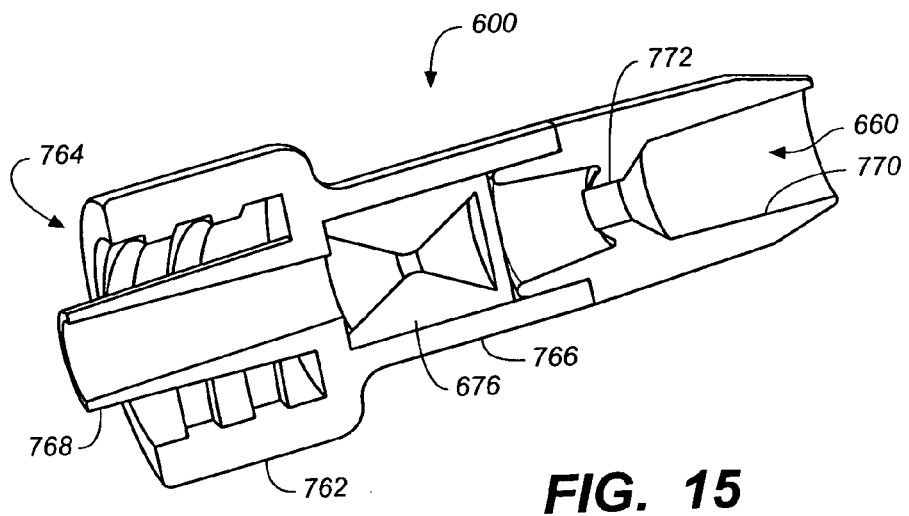
FIG. 15 illustrates another variation a detachable multifunction adaptor including a male luer-lock interface. The male luer-lock interface allows the user to connect the multifunction adaptor onto a female luer at the proximal end of a catheter.

In another variation, the multifunction adaptor includes a locking collar or ring at the distal end of the housing (e.g., luer lock interface, etc.) for engaging a female luer connector interface at a proximal end of a catheter. FIG. 15 illustrates one example where the multifunction adaptor 600 is configured with a threaded locking collar 762, which is positioned around a luer slip 768 at the distal end 764 of the adaptor housing 766. A valve 676 is positioned within the lumen 660 of the housing 766 to modulate fluid flow. In this particular example, an hourglass-shaped slit valve 676 is positioned within the housing 766. The proximal portion of the lumen may be configured with a luer-type surface 770 for receiving a syringe. An additional locking interface 772 may also be provided within the lumen 660 of the housing for engaging a tunneler.

In another variation, the locking collar or ring is configured such that it can freely rotate in relation to the housing of the multifunction adaptor. The free rotating collar/ring design may provide various advantages including, for example, cheaper manufacturing cost due to simplified molds and the ability of the multifunction adaptor to be attached/detached without rotating the entire structure. However, a fixed collar design may also provide various advantages including, for example, that the adaptor can be attached/detached without the need to isolate the collar/ring at the distal end of the adaptor and that the assembly of the device is simplified due to fewer parts.

In another variation, the proximal end of the multifunction adaptor is configured with a threaded luer connection interface. In another design, the proximal end of the adaptor housing includes ears extending radially for engaging a male luer lock fitting. In yet another design, the housing of the adaptor comprises two halves that are jointed together to secure an hourglass-shaped slit valve. The two halves of the housing can be joined in a variety of manners, including, but not limited to, solvent bonding, adhesive bonding, ultrasonic welding, or mechanical interlocking.

Figure 16A:
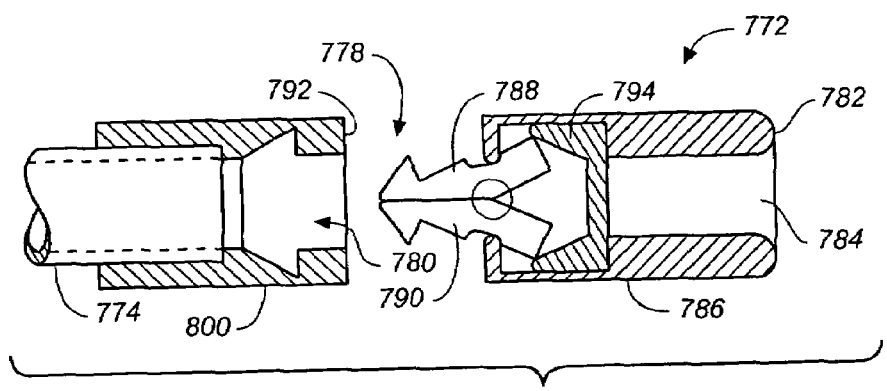
FIG. 16A illustrates an adaptor configured for coupling a tunneler to the proximal end of a catheter.
Figure 16B:
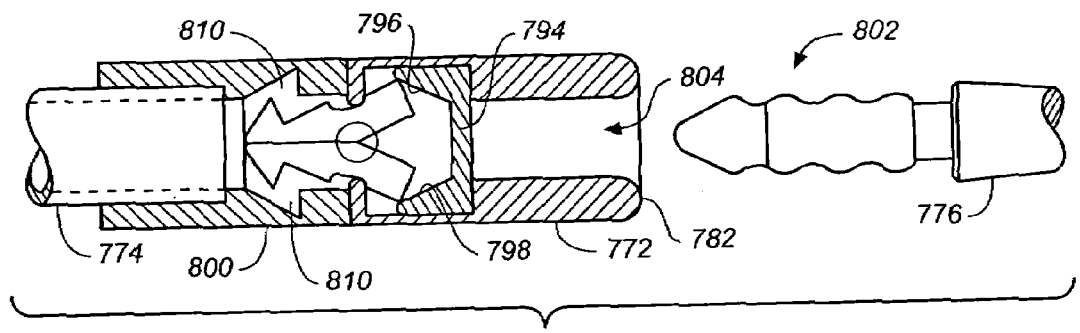
FIG. 16B illustrates the adaptor of FIG. 16A inserted within its corresponding catheter, and the proximal barbed end of a tunneler is positioned for insertion into the adaptor.

In another aspect of the invention, an adaptor 772 is provided for connecting the proximal end of a catheter 774 to a tunneler. In one variation, the adaptor 772 comprises an expandable locking mechanism 778 for engaging the inner lumen of a catheter 774 to secure the adaptor 772 onto the proximal end of the catheter 774. The proximal end 782 of the adaptor is configured with a receptacle 784 to receive and engage a tunneler 776. In one example, as shown in FIG. 16A, the adaptor 772 comprises a housing 786 supporting a pair of pivoting barbs 788, 790, which can be inserted into the proximal end 792 of a catheter 774 to secure the catheter. An anvil 794 is slidably disposed within the adaptor housing 786. The distal portion of the anvil comprises two tapered surfaces 796, 798 for engaging pivoting barbs 788, 790. The proximal end of the catheter is connected to a connector hub 800 for receiving the distal ends of the pivoting barbs 788, 790. FIG. 16B shows the pivoting barbs 788, 790 in a collapsed position, which allows them to be inserted into the proximal opening of the connector hub 800. The barbed end 802 of tunneler 776 is shown aligned with the proximal opening of the adaptor 772 for insertion into the lumen 804 of the adaptor 772.

Figure 16C:
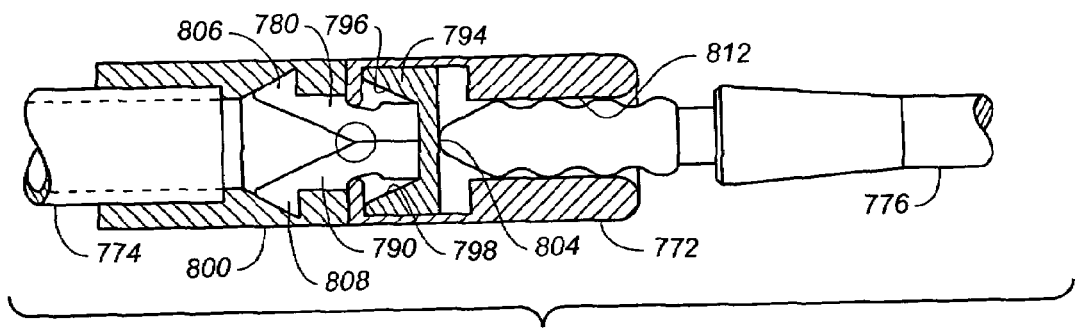
FIG. 16C illustrates the tunneler from FIG. 16B inserted into the adaptor, forcing the locking mechanism on the adaptor to engage the catheter, thus, securing the catheter to the tunneler.

FIG. 16C illustrates the tunneler 776 being inserted into the adaptor 772. As the tip 804 of the tunneler 772 engages proximal surface on the anvil 794, the anvil 794 is displaced in the distal direction. The two tapered surfaces 796, 798 on the distal side of the anvil 794 engage the proximal ends of the pivoting barbs 788, 790 and force the pivoting barbs 788, 790 to rotate in opposite directions, leading to the distal barbed ends of the pivoting barbs to spread and engage the inner lumen surface of the connector hub 800. The inner lumen surface of the connector hub 800 is configured with a notch 810 or an indentation to receive the barbed surface on the pivoting barbs 788, 790. The inner lumen surface 812 of the adaptor 772 compresses against the barbs 802 on the tunneler 776 and secures the tunneler 776 to the adaptor 772, allowing the user to displace the proximal end of the catheter 774 by simply pulling on the tunneler 776.

In one variation, the inner lumen surface 812 of the adaptor 772 is configured with a surface profile (e.g., threaded surface, indentations, notches, etc.) for engaging the tunneler. Furthermore, a compression and/or expansion mechanism may be provided to force the pivoting barbs back into the collapsed position after the tunneler is pulled out of the adaptor. For example, a rubber O-ring may be provided around the distal portion of the pivoting barb, or a spring (e.g., spring loop, expandable metal piece, etc.) may be placed between the distal portions of the pivoting barbs, to return the distal ends of the pivoting barbs back into the original collapsed position once the tunneler is removed. With the pivoting barb in the collapsed position, the user can remove the adaptor and insert an extension tubing or bifurcating adaptor onto the proximal end of the catheter. In another application, once the tunneling of the proximal portion of the catheter is completed, the user may simply remove the tunneler by cutting off a distal portion of the catheter along with the connector hub and the attached adaptor.

In another aspect of the invention, a clip-ring 820, which may be a complete ring or a partial ring, is provided for placement over the barbed end 824 of a tunneler 826. The application of a clip-ring can improve the griping capability of the tunneler 826 when the tunneler is placed within a lumen of a catheter or a connector hub. The clip-ring may also be utilized to allow the user to connect a catheter or connector hub having a lumen that is large than the diameter of the barb on the tunneler. The clip-ring may be clipped onto or screwed onto the barbed end of the tunneler. The clip-ring may comprise of a metallic material, a polymeric material, or a combination thereof.

Figure 17A:
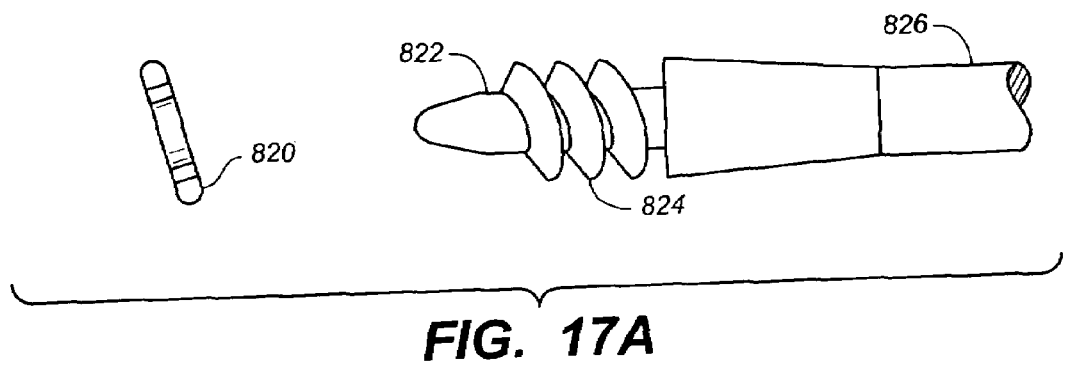
In FIG. 17A, the adaptor is shown detached from the catheter.
Figure 17B:
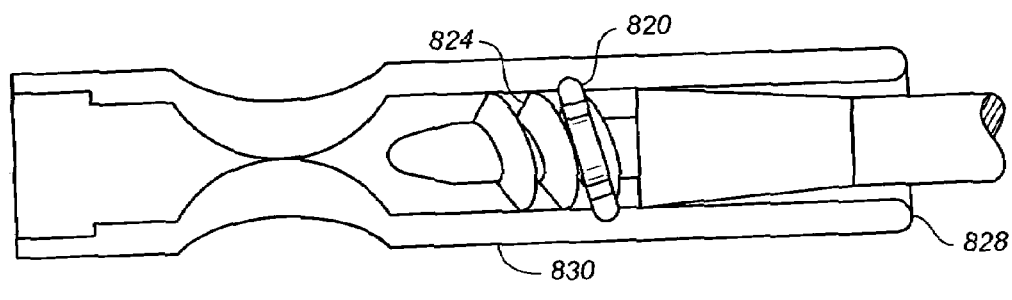
FIG. 17B illustrates the clip-ring of FIG. 17A inserted on the barb of the tunneler, and the barb along with the coupled clip-ring are inserted within the lumen of a connector hub.
Figure 17C:
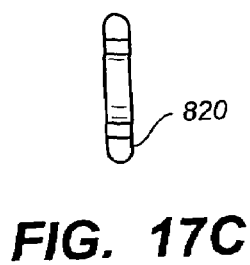
FIG. 17C shows a side view of the clip-ring from FIG. 17A
Figure 17D:
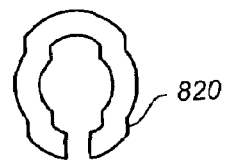
FIG. 17D shows a frontal view of the clip-ring of FIG. 17C.

FIG. 17A shows an example of a clip-ring 820, which is configured for placement over the barbed surface on the proximal end 822 of a tunneler 826. In this example, the clip-ring 820 comprises stainless steel. FIG. 17C shows the side view of the clip-ring 820, while FIG. 17D shows the front view on the clip-ring 820. The clip-ring, in this example, is configured with a "C" shaped structure and exhibits a semi-elastic, spring-like characteristic.

In one variation, the clip ring is designed to be over-molded or fitted into a connector hub 830 to form an assembly for receiving a tunneler. The tunneler 826 can then be inserted into the proximal end 828 of the connector hub 830, and pushed or screwed into the clip-ring 820 within the connector hub 830, as shown in FIG. 17B. The barb 824 on the tunneler engages the clip ring and secures the tunneler 826 to the connector hub 830. A catheter may be permanently attached to the distal end of the connector hub. In another variation, the connector hub is configured for temporary attachment to the proximal end of a catheter.

With the proximal end of the catheter coupled to the tunneler through the connector-hub/clip-ring assembly, the user can pull a proximal portion of the catheter through a subcutaneous channel. Once the proximal portion of the catheter has been tunneled through the subcutaneous channel, the tunneler is unscrewed from the clip-ring and removed from the lumen of the of the connector hub. In another approach, the tunneler along with the attached connector hub can be cut off and discarded, leaving the catheter with an open-ended proximal end for connection to an adaptor or a fluid/suction source.

In another variation, the clip-ring can be screwed onto the barb on a tunneler. The tunneler/clip-ring unit is then inserted into a catheter tubing or a connector hub, which is coupled to a catheter. Once the catheter has been tunneled, the user may remove the tunneler by unscrewing the tunneler, or by cutting off a portion of the catheter connected to the tunneler.

This invention has been described and specific examples of the invention have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed as new and desired to be protected by Letters Patent of the United States is:

1. An adaptor, comprising:
   a housing including a passageway extending therethrough, a distal opening for engaging a proximal end of a catheter, and a proximal portion of the passageway including a means for engaging a first end of a tunneler; and
   a valve comprising a closed proximal end including a slit and an open distal end, the closed proximal end positioned in the passageway distal of the means for engaging, a wall including an inner surface that defines a lumen connecting the proximal and distal ends of the valve, the inner surface of the wall narrowing from the valve proximal end to a valve mid portion and enlarging from the valve mid portion to the valve distal end, the wall configured to guide a proximal end of a guidewire from the valve distal end through the slit.

2. The adaptor according to claim 1, wherein the valve comprises a polymeric material having a hardness in the range of approximately 40 Shore A to approximately 60 Shore A.

3. The adaptor according to claim 1, wherein the means for engaging comprises a compression mechanism positioned in the passageway.

4. The adaptor according to claim 3, wherein the compression mechanism comprises a compression sleeve or a locking disk.

5. The adaptor according to claim 1, wherein the proximal portion of the passageway includes a wall with a tapered surface, the means for engaging comprising a raised surface profile on the wall distal of the tapered surface.

6. The adaptor according to claim 5, further comprising a locking disk positioned in the passageway configured to mechanically engage a second end of a tunneler different from the first end.

7. The adaptor according to claim 1, wherein the housing further comprises a barb-shaped locking interface at the distal end of the housing.

8. An adaptor in combination with a tunneler, comprising:
   a passageway including a proximal portion having a means for engaging a first end of the tunneler and a means for engaging a second end of the tunneler, different from the first end of the tunneler, the means for engaging the second end of the tunneler positioned distal of the means for engaging the first end of the tunneler; and
   a valve including a closed proximal end with a slit positioned distal of the means for engaging the second end of the tunneler.

9. The adaptor according to claim 8, wherein the valve includes an open distal end and a lumen that narrows from the valve proximal end to a mid portion of the lumen and expands from the mid portion of the lumen to the valve distal end.

10. The adaptor according to claim 8, wherein the means for engaging the first end of the tunneler comprises a raised surface profile on a wall of the passageway.

11. The adaptor according to claim 8, wherein the means for engaging the second end of the tunneler comprises a locking disk including a center opening.

12. The adaptor according to claim 8, wherein a wall of the passageway proximal to the means for engaging the first end of the tunneler is tapered to receive a male luer and form a friction fit therewith.

13. The adaptor according to claim 8, wherein a distal end of the adaptor includes a locking interface configured to engage a connector hub.

14. The adaptor according to claim 13, further comprising a catheter with a proximal end attached to the connector hub, connection of the adaptor to the connector hub establishing fluid communication between the passageway and a lumen of the catheter.

15. An adaptor in combination with a tunneler and catheter, comprising:
   a passageway including a proximal portion having separate first and second engagement features respectively connecting first and second ends of the tunneler to the adaptor, wherein the first and second ends of the tunneler have different configurations;
   a valve positioned in a distal portion of the passageway including a proximal end biased in a closed configuration, the proximal end positioned distal of the first and second engagement features; and
   a barbed locking interface extending from a distal end of the adaptor for insertion into a connector hub attached to a proximal end of the catheter, the connector hub including a notch for engaging the locking interface.

* * * * *